United States Patent
Haschtmann et al.

(10) Patent No.: US 12,383,309 B2
(45) Date of Patent: Aug. 12, 2025

(54) SPINAL BONE FASTENER ASSEMBLY

(71) Applicant: INNO4SPINE AG, Stans (CH)

(72) Inventors: Daniel Haschtmann, Küsnacht (CH); Heiko Koller, Kufstein (AT); Dezsö János Jeszenszky, Küsnacht (CH); Tamás Fülöp Fekete, Zürich (CH); Adriano Viganò, Pfäffikon (CH)

(73) Assignee: INNO4SPINE AG, Stans (CH)

( * ) Notice: Subject to any disclaimer, the term of this patent is extended or adjusted under 35 U.S.C. 154(b) by 430 days.

(21) Appl. No.: 17/921,512

(22) PCT Filed: Mar. 1, 2021

(86) PCT No.: PCT/IB2021/051686
§ 371 (c)(1),
(2) Date: Oct. 26, 2022

(87) PCT Pub. No.: WO2021/140498
PCT Pub. Date: Jul. 15, 2021

(65) Prior Publication Data
US 2023/0172641 A1    Jun. 8, 2023

(30) Foreign Application Priority Data
Mar. 3, 2020   (CH) ..................................... 00251/20

(51) Int. Cl.
*A61B 17/70*     (2006.01)
(52) U.S. Cl.
CPC ........ *A61B 17/7037* (2013.01); *A61B 17/705* (2013.01)
(58) Field of Classification Search
CPC ............ A61B 17/7032; A61B 17/7034; A61B 17/7035; A61B 17/7037; A61B 17/7041;
(Continued)

(56) References Cited

U.S. PATENT DOCUMENTS

| 8,998,961 B1 | 4/2015 | Ziemek et al. |
| 2007/0093819 A1* | 4/2007 | Albert ................ A61B 17/7034 606/278 |

(Continued)

FOREIGN PATENT DOCUMENTS

| EP | 3366240 A1 | 8/2018 |
| WO | 2017127647 A1 | 7/2017 |

OTHER PUBLICATIONS

CH Search Report in application No. CH 00251/20 dated Jun. 9, 2020.

(Continued)

*Primary Examiner* — Eduardo C Robert
*Assistant Examiner* — Michelle C Green
(74) *Attorney, Agent, or Firm* — Maschoff Brennan

(57) ABSTRACT

A spinal bone fastener assembly connects or aligns at least two rods and includes a bone fastener having a bone fastener head and a bone fastener shaft with a shaft axis. The assembly further includes an elongated connector head for receiving the two rods, at least one rod fastener, at least one bone fastener engaging insert and/or at least one rod receiving inlay. The connector head includes one rod receiving passage extending longitudinally or at least two rod receiving passages extending sideways through the elongated connector head. The connector head also includes an elongated bone fastener head receiving recess, which is open to the head bottom side, and at least one locking feature for engaging with the rod fastener. The recess provides at least one translational degree of freedom for the bone fastener, and at least one rotational degree of freedom for the bone fastener around the shaft axis.

29 Claims, 25 Drawing Sheets

(58) Field of Classification Search
CPC .... A61B 17/7043; A61B 17/7049–705; A61B 17/7052
See application file for complete search history.

(56) References Cited

U.S. PATENT DOCUMENTS

| | | | |
|---|---|---|---|
| 2011/0106166 A1* | 5/2011 | Keyer | A61B 17/7034 606/279 |
| 2014/0052195 A1 | 2/2014 | Vargas Soto | |
| 2015/0182261 A1* | 7/2015 | Lovell | A61B 17/7037 470/6 |
| 2015/0359568 A1* | 12/2015 | Rezach | A61B 17/7032 606/266 |
| 2019/0046241 A1 | 2/2019 | Leff et al. | |
| 2019/0105081 A1* | 4/2019 | Gregory | A61B 17/7041 |
| 2019/0290329 A1 | 9/2019 | Bess et al. | |

OTHER PUBLICATIONS

EP Office Action dated Jun. 4, 2024 as received in Application No. 21711037.8.

\* cited by examiner

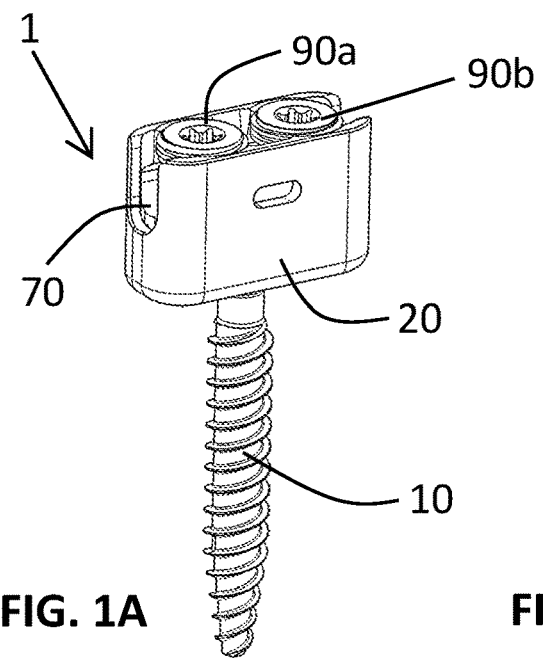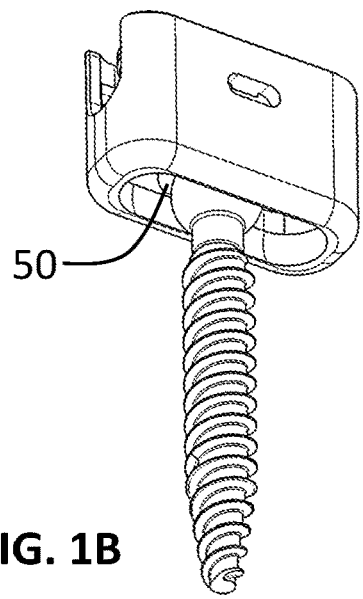
FIG. 1A  FIG. 1B
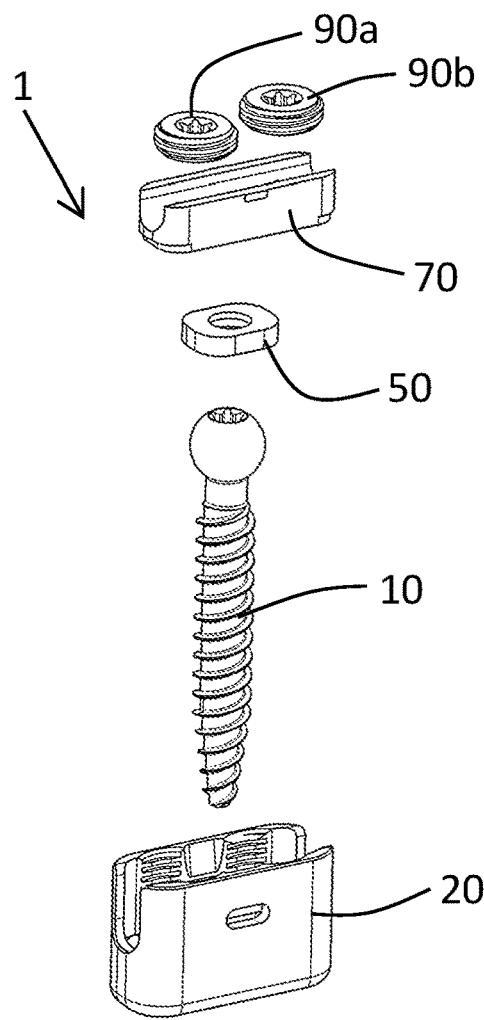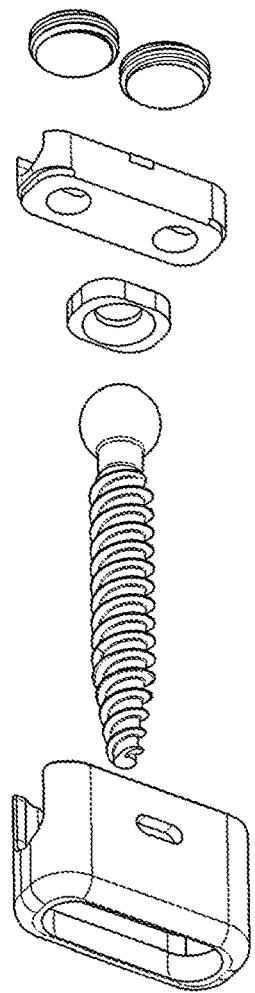
FIG. 2A  FIG. 2B

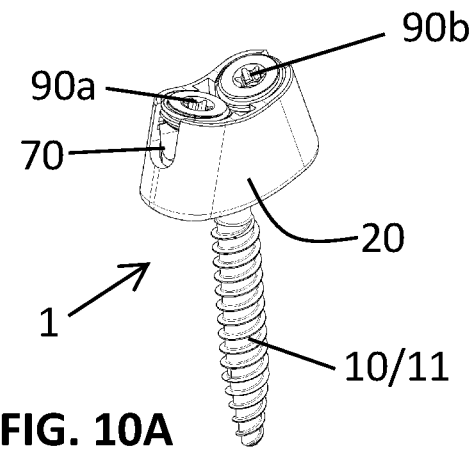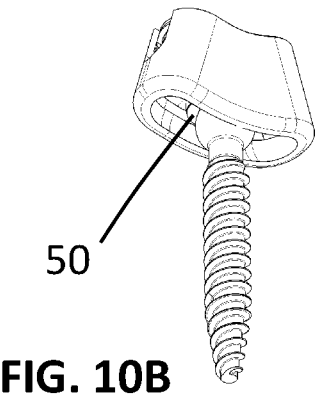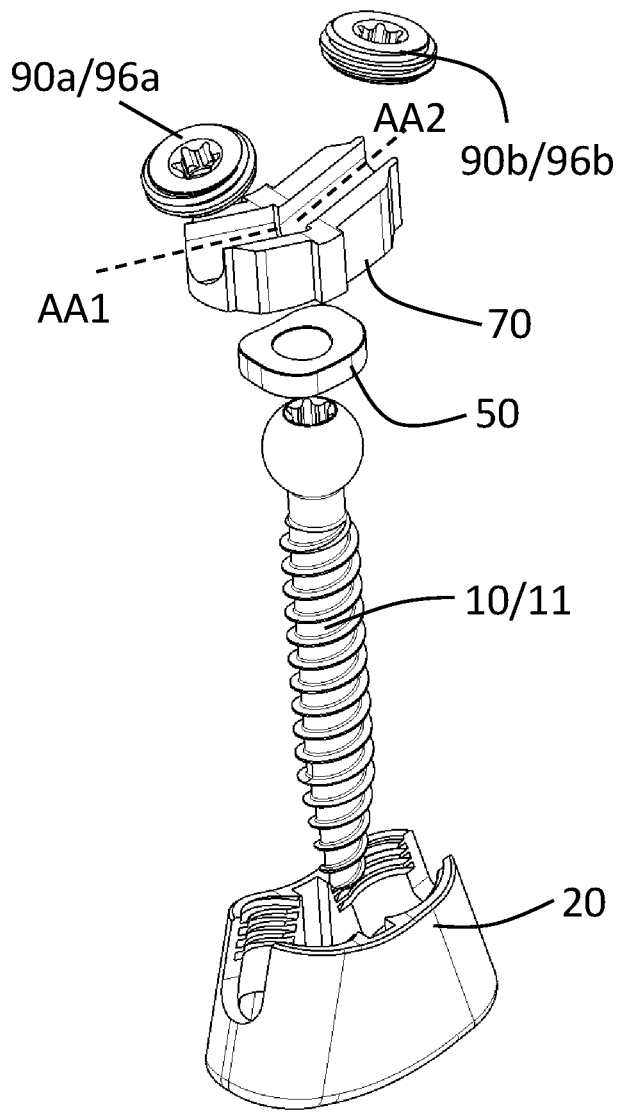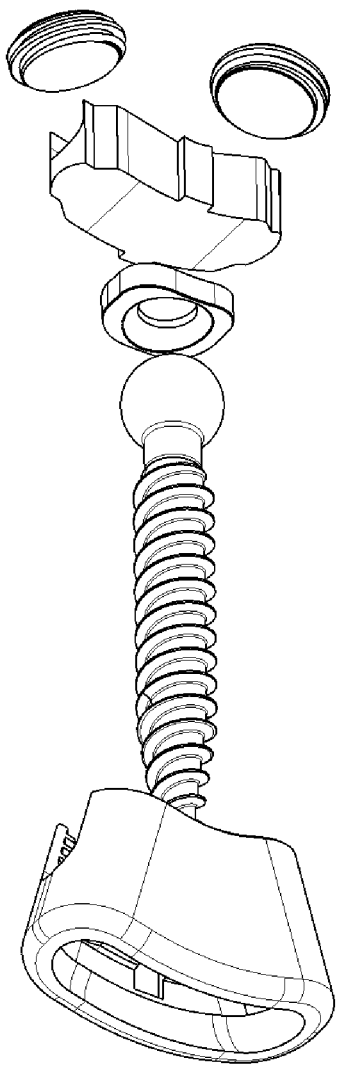
FIG. 10A
FIG. 10B
FIG. 10C
FIG. 10D

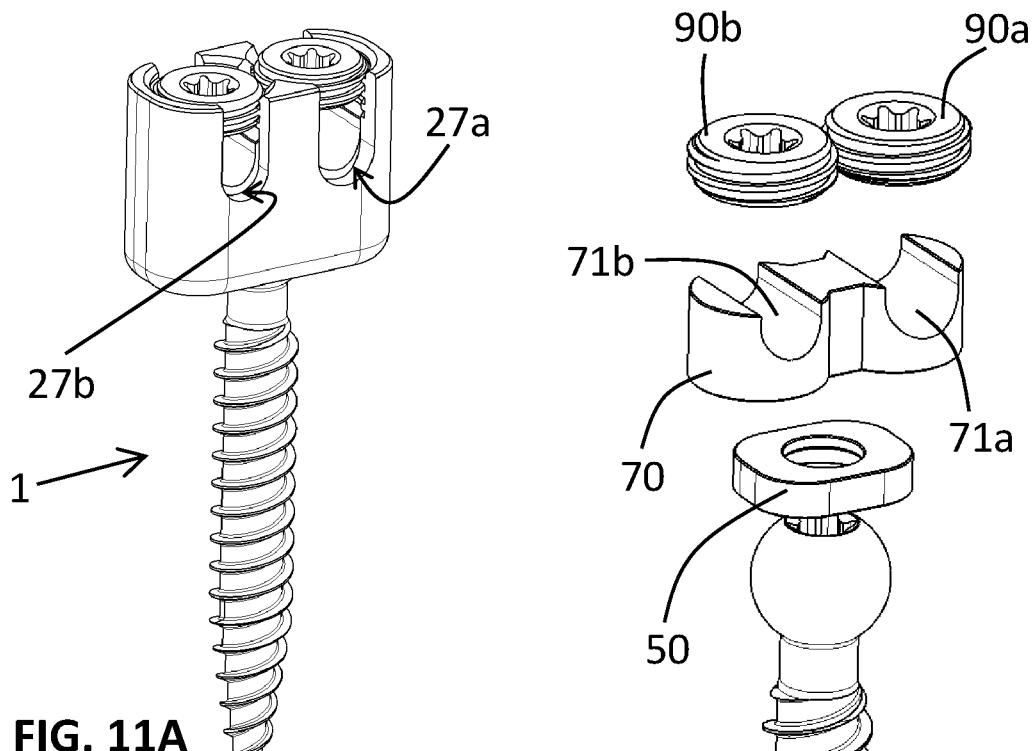
FIG. 11A
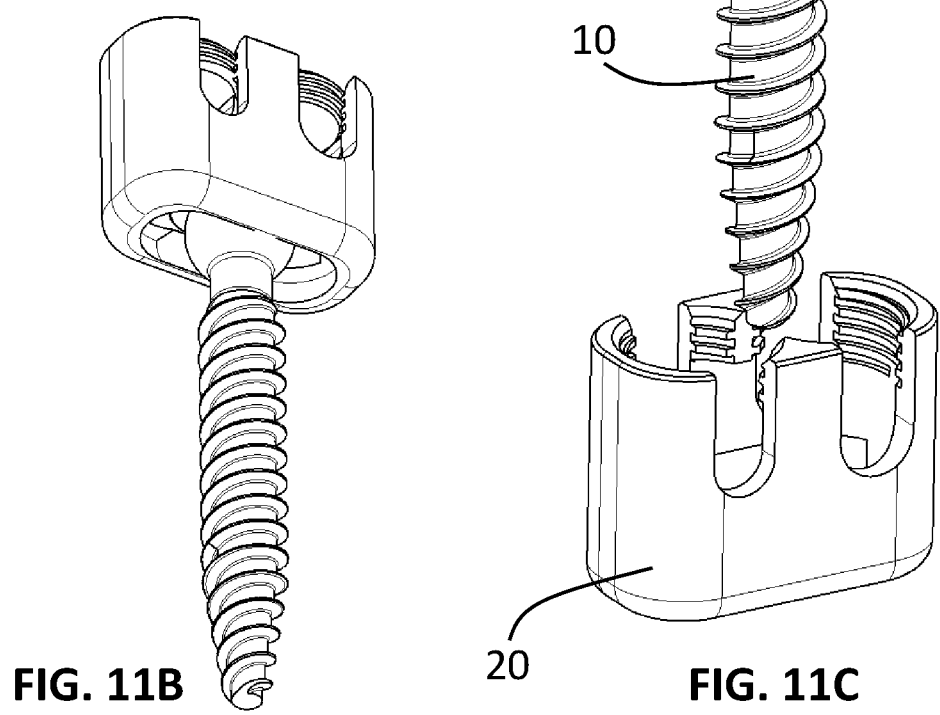
FIG. 11B
FIG. 11C

120b

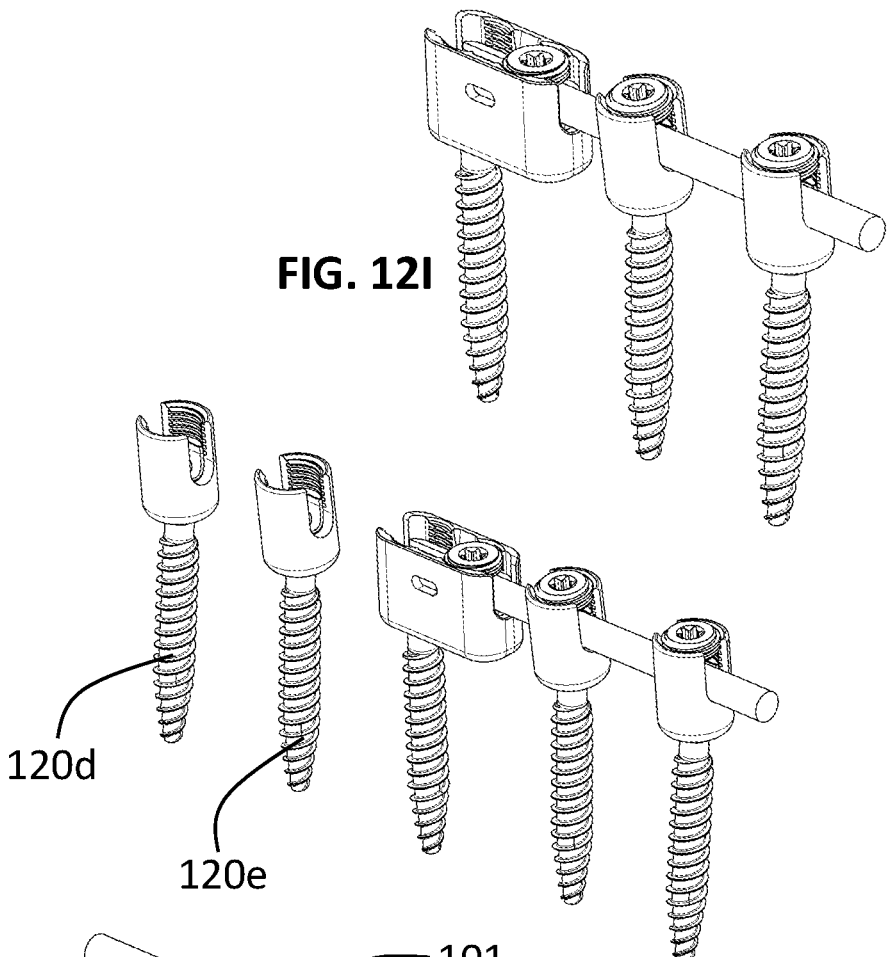
FIG. 12I
FIG. 12J
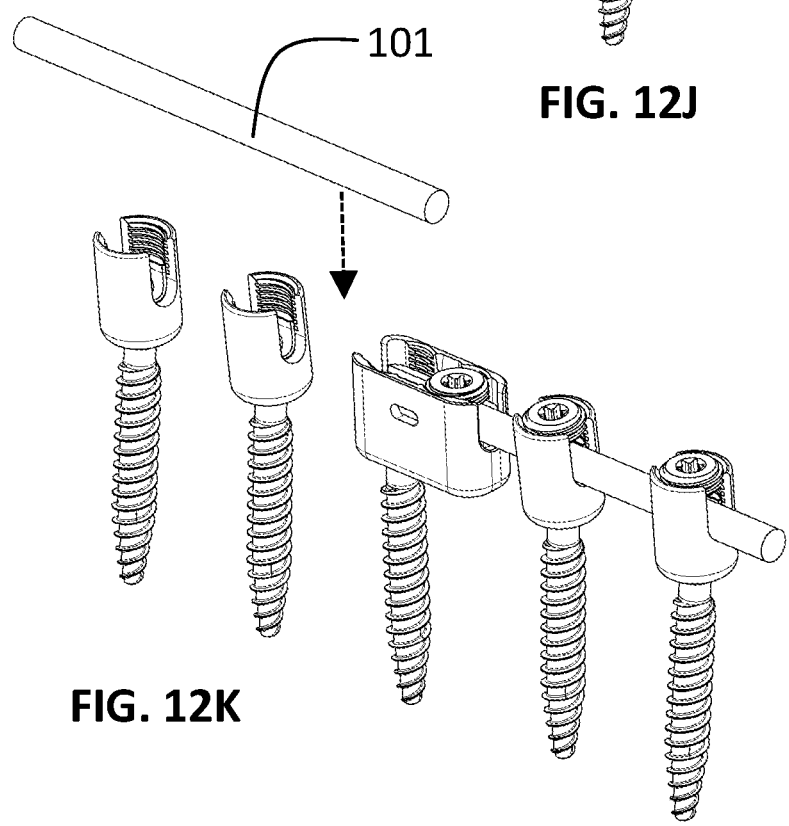
FIG. 12K

SPINAL BONE FASTENER ASSEMBLY

TECHNICAL FIELD OF THE INVENTION

The present invention relates to a spinal bone fastener assembly for elongating a spinal posterior rod system. The posterior rod system can be an in situ system that needs elongation, and it may further be a new system needing a transition between two different rod sizes (and shapes). In the case of an in situ system, surgical procedures may include removal of the last screw of an in-situ system. The present invention also relates to a method for connecting a spinal pedicle bone fastener assembly to an existing posterior spinal construct and for connecting to an additional spinal rod. The invention further relates to a kit containing multiple rod engaging inserts enabling connecting spinal rods of different diameters as well as rods of equal diameters or shapes.

BACKGROUND OF THE INVENTION

In orthopaedic surgery around the spine, posterior spinal stabilisation systems are often placed to a target site to realign, correct and/or stabilise the spinal column to compensate for malalignment caused by for example degeneration of the spine, born malalignments, such as excessive lordosis, kyphosis and scoliosis, and for example trauma, such as fractures.

Often a preplaced construct, or a construct in situ needs to be extended to different vertebral levels of the spinal column due to progression of the degeneration or disease, or due to stability reasons, namely failure of the construct. A construct is best extended in a substantial collinear orientation to the in situ construct. To be able to extend the construct, according to common techniques, a full in situ rod, which is part of the construct, is removed from bone fasteners, and replaced by a rod of longer length. Removal is executed by unscrewing so-called set screws that rigidly fix the rod into a tulip head of the bone fastener. The rod is pulled out after removal of all set screws. In an additional surgical step, new bone fasteners are placed in the vertebral levels, to which the construct is intended to be elongated.

Now, the new rod of longer length is reattached to the bone fasteners that are in place, and additionally attached to newly placed bone fasteners. The removal of the old rod destabilises the spine during surgery, and requires a large skin and soft tissue access to the implants. Especially in the cases of longer constructs, this can be a very invasive surgery. Alternatively, a new rod can collinearly be attached to the in situ rod. Also here the bone fasteners that are in place need to be manipulated. Some of the set screws which fixate the in situ rod to the bone fasteners, need to be loosened, to lift the in situ rod, and to attach a rod extension. Also this procedure requires one or more large skin and soft tissue access locations for the construct. Especially in the cases of longer constructs, this can equally be a very invasive surgery.

Two typical failure modes of an overloaded spinal construct exist, namely loosening of the fastener and breakage of the rod between two adjacent bone fasteners. Often, when an in situ construct needs an extension, this is due to a loosened last bone fastener of an in situ construct. The forces on the posterior stabilisation system have been so high that loosening of the bone fastener at the bone-screw interface occurred. In case of loosening, the loosened fastener needs to be replaced with a new, most often, thicker bone fastener, and additional fasteners need to be placed at a next vertebral level, requiring a longer rod and so providing the needed stability. In many cases extensions need to be placed to transition areas of the lumbar-to-thoracic and thoracic-to-cervical spine.

Anatomically, the natural spine decreases in size from the lumbar spine to the cervical spine (from the lower back to the neck). Therefore, when extending a system towards the cervical spine, there is a need for connecting the system to smaller rods. In most common spinal stabilisation systems, this transition is made using intermediate connectors which allow a thinner rod to be placed next to a thicker rod. The transition is created by connecting the ends of a thicker rod and a thinner rod in a parallel manner, resulting in a more voluminous construct. Furthermore, also in first or primary surgery, a construct may need to bridge a transition area of the spine, requiring the ability to connect thinner and thicker rods.

SUMMARY OF THE INVENTION

It is an object of the present invention to overcome at least some of the problems associated with elongating an existing pedicle screw and rod construct, for instance either during primary placement or revision surgery. In revision surgery, a solution is needed that, after removal of the last, often loosened bone fastener, allows the posterior construct to be extended and re-stabilised in a less invasive manner. Prior to removal of the bone fastener, the rod must be cut directly adjacent to the bone fastener. Therefore, there is a need for an assembly that obviates the need of removal of the in situ rod, which would destabilise the spine. Additionally, there is also a need for an assembly that provides the ability and flexibility to connect an existing rod to rods of substantially identical and different diameters. In the cases of primary surgery, a new system is needed that would allow the rod size to be increased or decreased at the level of the bone fastener, without adding large volume to the construct.

According to a first aspect of the invention, there is provided a spinal bone fastener assembly as recited in claim 1.

The proposed bone fastener assembly includes an elongated connector head and therefore can be connected to two rods. Moreover, the elongated connector head can be connected to a bone fastener in such a way that the bone fastener can slide along the length of the elongated connector head, and allows the surgeon to slide the connector head under an in situ rod.

According to a second aspect of the invention, there is provided a kit comprising a spinal pedicle bone fastener assembly, wherein the kit comprises multiple inserts, wherein the inserts are sized and shaped to receive rods of different diameters and/or shapes. During the surgery, the surgeon can assemble the insert within the elongated connector head, and adapt the pedicle bone fastener assembly to the required rod diameters.

According to a third aspect of the invention, there is provided a method for connecting a spinal bone fastener assembly to an implanted spinal construct as recited in claim 28.

BRIEF DESCRIPTION OF THE DRAWINGS

Other features and advantages of the invention will become apparent from the following description of non-limiting example embodiments, with reference to the appended drawings, in which:

FIGS. 1A and 1B depict in perspective views an example bone fastener assembly according to an embodiment of the present invention;

FIGS. 2A and 2B depict the bone fastener in exploded views;

FIGS. 10A to 10D depict one further alternative design of the bone fastener assembly in detail, where the bone fastener assembly is curved or bent;

FIGS. 11A to 11C depict one further alternative design of the bone fastener assembly in detail, where the bone fastener assembly is configured to receive two rods placed parallel;

DETAILED DESCRIPTION OF THE INVENTION

Figure 3:
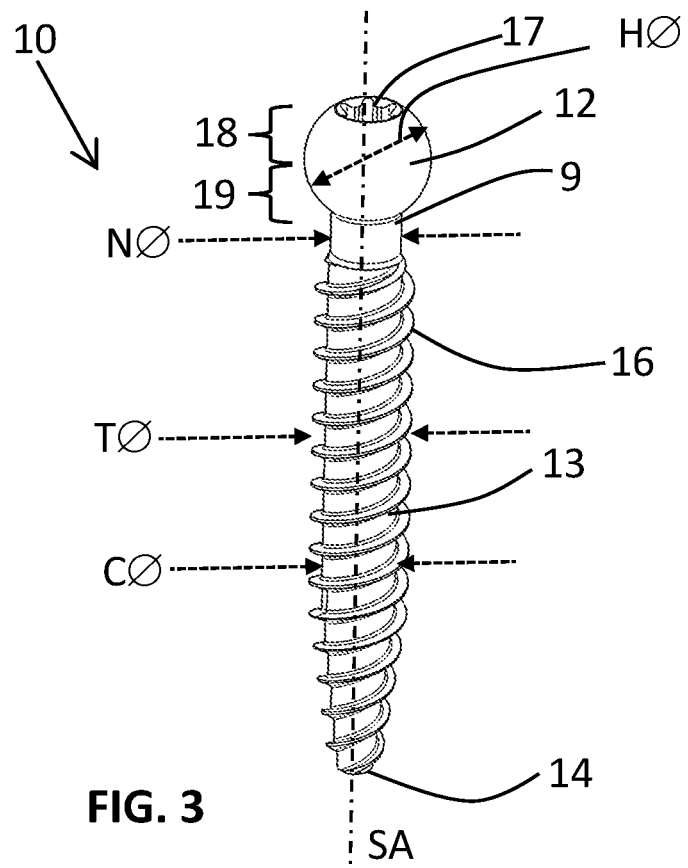
FIG. 3 depicts the bone fastener or bone screw of the bone fastener assembly in detail.
Figure 4A:
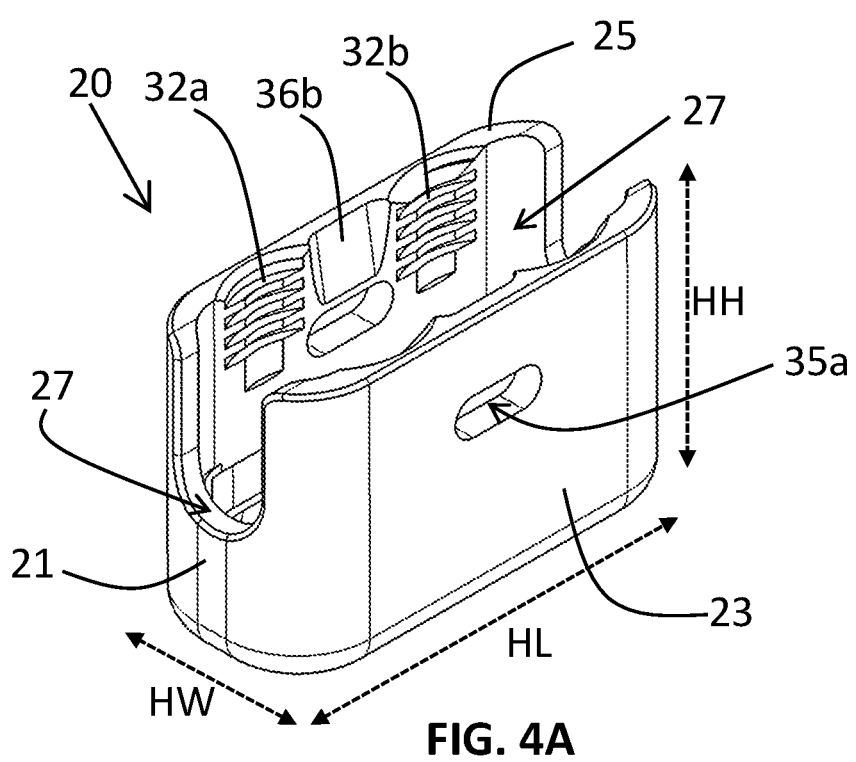
FIGS. 4A to 4D depict the elongated connector head of the bone fastener in detail.
Figure 4B:
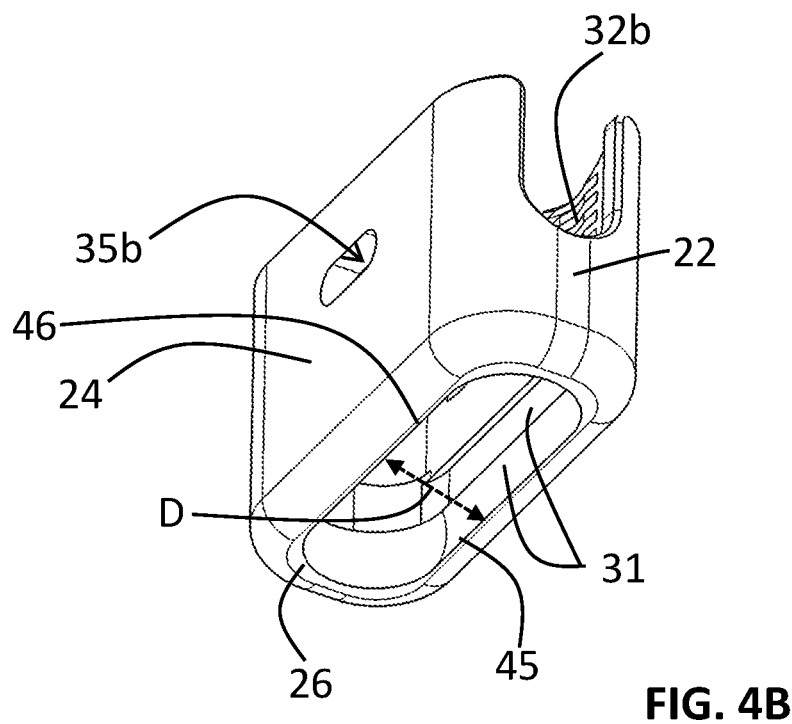
Figure 4C:
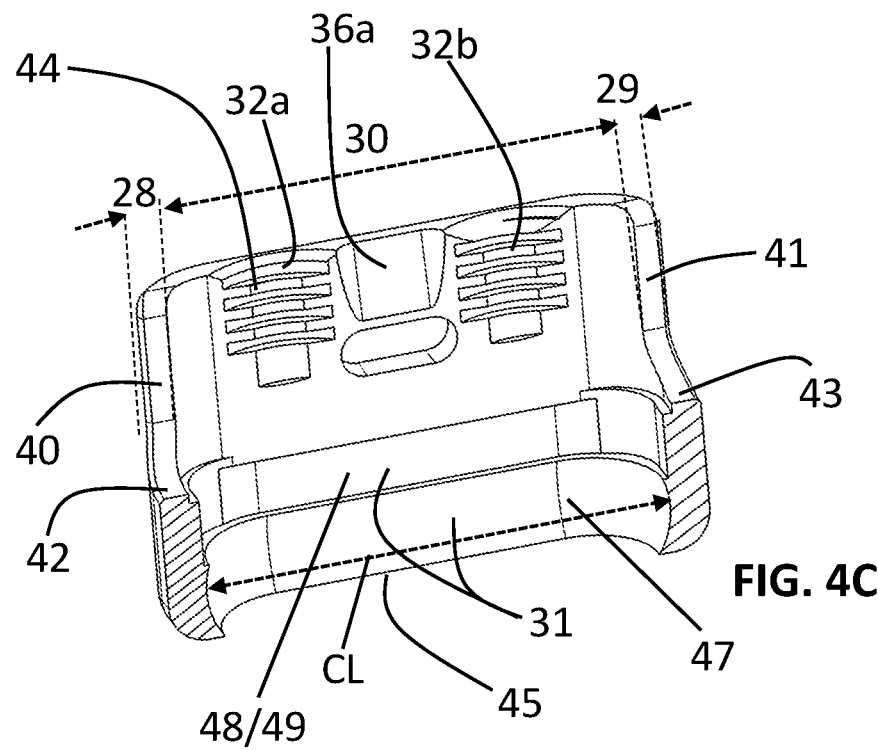
Figure 4D:
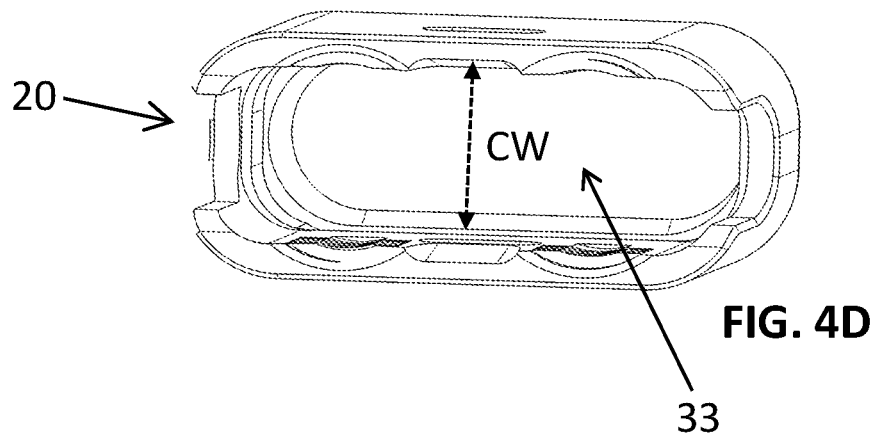

The embodiments of the present invention will now be described in detail with reference to the attached figures. The embodiments are described in the context of extending or elongating an in situ posterior spinal construct. Although the invention is specifically described in the context of extending the posterior spinal construct, the teachings of the invention are not limited to this environment. The teachings of the present invention are equally applicable to extending rod-based stabilisation constructs for other bones. When the words first and second are used to refer to different elements, it is to be understood that this does not necessarily imply or mean that the first and second elements are somehow structurally substantially different elements or that their dimensions are substantially different unless specifically stated. A bone fastener in this context means a structural element, which can be brought into the target bone, and forms a stabile connection between the target bone and the remaining spinal construct. Most often, a bone fastener is a fastening element, such as a pedicle screw. Identical or corresponding functional and structural elements which appear in the different drawings are assigned the same reference numerals.

Referring to FIGS. 1A, 1B, 2A and 2B, a bone fastener assembly 1 according to an example of the present invention is shown in two perspective views and two exploded views. The bone fastener assembly comprises a bone fastener 10, or more specifically a pedicle screw, a connector head 20, which in this example is elongated, a bone fastener engaging insert 50, a rod receiving inlay 70 and at least one rod fastener 90a, 90b, such as a set screw. The bone fastener assembly is configured to receive at least one, more preferably two state-of-the-art spinal posterior stabilisation rods, or rods 100, 101, as described in greater detail later.

The bone fastener 10, which in this example is a pedicle screw, is shown in a perspective view in FIG. 3. The bone fastener comprises an elongated shaft 13 extending between the tip 14 and a bone fastener head 12. As depicted, the bone fastener head is in this example a spherical head, and the shaft comprises an external thread 16. At a transition region, where the shaft 13 transitions into the spherical head 12, a neck section 9 is present. The spherical head further comprises a drive 17 for engagement with a tool, such as a screwdriver. The spherical head is divided in a top half 18, and a bottom half 19 and defines a spherical head diameter HØ. The elongated shaft 13 defines a neck section diameter NØ, a shaft core diameter CØ, and a thread outer diameter TØ. A shaft axis SA extends longitudinally across the shaft or the entire screw.

Referring to FIGS. 4A to 4D, the elongated connector head 20 is shown in greater detail. The connector head has a (horizontal) head length HL, a (horizontal) head width HW and a (vertical) head height HH, which in this example are dimensions orthogonal to each other, where the head width HW and head height HH collectively define a first head end 21 and a second, opposite head end 22, which are longitudinally at opposite ends of the connector head, the head length HL and head height HH collectively define a first head side 23 and a second, opposite head side 24, and the head length HL and head width HW collectively define a head top side 25 and an opposite head bottom side 26.

A head length (HL) to head width (HW) ratio (HL:HW) may be at least 1.5:1, and more specifically at least 1.8:1. The elongated connector head is depicted as a substantially block-shaped body, having rounded edges. It is to be noted that in order to reduce any soft tissue irritation, implant portions, such as the elongated connector head, have rounded, chamfered or broken edges. The elongated connector head 20 further comprises a rod receiving passage 27 extending between the first head end 21 and the second head end 22, and which in this example is at least partially open to the head top side 25. Thus, the rod receiving passage forms a clearance to the head top side through which the rods can be placed, prior to placement and tightening of the rod fasteners. More specifically, the rod receiving passage comprises a passage start section 28, a passage end section 29, and a passage middle section 30. The passage start and end sections are formed by a first end wall 40 and a second end wall 41, respectively. The passage end sections each comprise a passage bottom 42, 43. According to this example, the rod receiving passage 27 extends lengthwise or longitudinally across or through the elongated connector head 20. At the head top side, the elongated connector head comprises at least one locking means or feature 32a, 32b, sized and shaped to receive and/or engage with at least one rod fastener 90a, 90b. In the present example, the locking means is configured as an internal thread portion or feature

44. In the examples shown in the figures, the elongated connector head 20 comprises two locking features or internal threads arranged side by side, longitudinally along a longitudinal axis of the connector head, and configured to engage with a respective rod fastener.

As depicted in FIGS. 1A, 1B, 2A and 2B, the bone fastener 10 is assembled into the elongated connector head through the head top side 25 so that the bone fastener shaft 13 protrudes through the head bottom side 26. In order to receive the bone fastener, and more specifically the bone fastener head 12 or a portion of it, the elongated connector head comprises a bone fastener head receiving recess 31, which is open to the head bottom side 26. The recess 31 may be sized and shaped to receive the bone fastener head 12 or a portion of it directly, and/or it may receive an intermediate insert, which is configured to receive the bone fastener head directly.

As depicted in FIGS. 4A to 4D, the recess 31 is configured as a combined elongated channel, including a channel top portion 48 and a channel bottom portion 47. The channel top portion is configured to receive the bone fastener engaging insert 50, where the channel bottom portion 47 is configured to engage directly with the spherical head 12, in such a manner that it encompasses the bone fastener head bottom half 19 and inhibits separation of the bone fastener head out of the elongated channel. The elongated channel has an average channel length CL and an average channel width CW. As depicted, the combined elongated channel extends into the head bottom side, therefore forming a first recess margin 45 and second recess margin 46 at opposing sides of the connector head 20 and thus forming an opening for the screw shaft 13. The first and second recess margins 45, 46 are oriented substantially parallel to the length of the elongated connector head. The first and second recess margins 45, 46, are spaced at an average distance D. In one embodiment, the average distance D is smaller than the head diameter HØ and greater than the neck section diameter NØ of the bone fastener 10. The ratios between the distance D, the head diameter HØ and the shaft core diameter CØ define the angular range of motion of the bone fastener within the bone fastener head receiving recess 31, or in other words, the number of degrees the bone fastener can angulate, swivel or pivot sideways, i.e., for example along a direction defined by the longitudinal axis of the elongated connector head. The angulating, pivoting or swivelling action may in some examples be possible around a rotation angle of 360 degrees. It is to be noted that that depending on the design of the connector head and/or on the locking force of the rod fasteners 90a, 90b, the pivoting or swivelling action relative to the elongated connector head may only be possible when the bone fastener assembly 1 is in a non-locked configuration as opposed to a locked configuration in which the different elements of the bone fastener assembly are firmly locked in place with the rod fasteners 90a, 90b. Furthermore, as depicted, the channel length CL is significantly longer than the head diameter HØ of the bone fastener 10. Therefore, in addition to swivelling, and turning about its axis, the bone fastener can translate, optionally only in the non-locked configuration, along the length of the elongated channel. According to one example, the translational degree of freedom of the fastener head within the elongated channel is at least 6 mm, or more specifically at least 10 mm.

The channel top portion 48 is sized and shaped to receive the bone fastener engaging insert 50. In the design shown in FIGS. 4A to 4D, the top channel portion is shaped as a groove 49, bilaterally extending along the length of the elongated channel. The groove 49 has a height which is greater than the thickness of the insert, allowing minimal vertical translation of the insert within the groove as explained in greater detail later. As depicted, the elongated channel is located between the first and second head ends 21, 22. According to a variant of the invention, the elongated channel 31 extends at least into one of the first and second head ends 21, 22.

The elongated connector head further comprises a pocket 33 extending from the head top side 25 into the head bottom side 26. The pocket 33 intersects the rod receiving passage 27, the locking means 32a, 32b and the bone fastener head receiving recess 31. The pocket 33 is sized and shaped to receive the rod receiving inlay 70. The inner wall of the pocket therefore is shaped in a substantially complementary manner in relation to the inlay outer shape. According to the present example, the pocket encompasses the inlay 70 in such a manner that the major available degree of freedom is the possibility for the inlay to translate vertically. i.e., substantially along the length axis of the screw shaft or parallel to that axis. As depicted, the elongated channel 31 is located between the first and second head ends. According to a variant of the invention, the elongated channel 31 extends at least into one of the first and second head ends 21, 22. The illustrated elongated connector head also comprises one or more cut-outs 35a, 35b, e.g. one cut-out per connector head side, and a bevelled inlet 36a, 36b, e.g. one bevelled inlet per connector head side. The cut-outs 35a, 35b are intended to inhibit unwanted dislodgement of the inlay 70 out of the elongated connector head as explained later. The cut-outs can also be used as an instrument attachment feature. The bevelled inlet facilitates the assembly of the inlay 70.

Figure 5A:
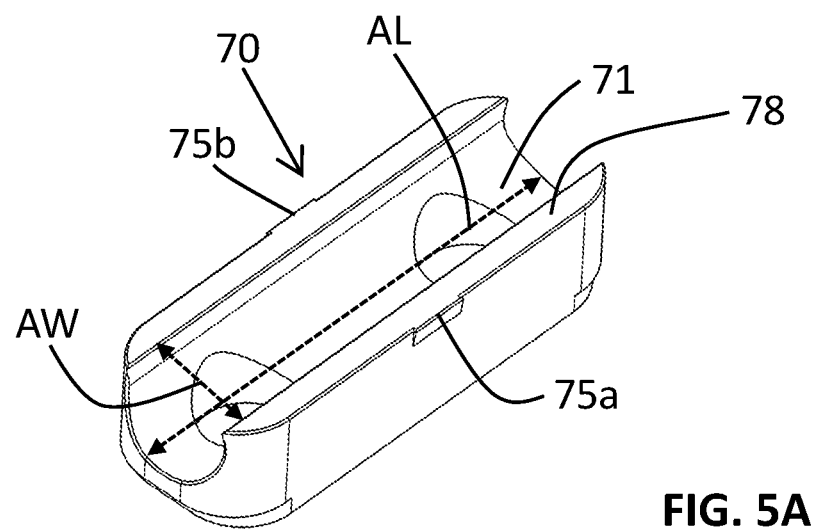
FIGS. 5A to 5D depict a rod receiving inlay in detail.
Figure 5B:
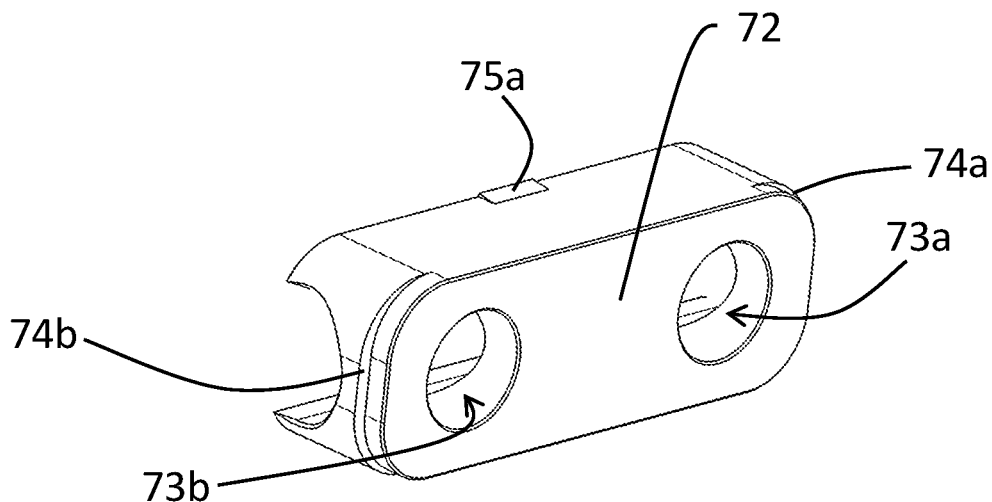

FIGS. 5A to 5D show designs of the rod receiving inlay or insert 70 in greater detail. FIGS. 5A and 5B depict the basic insert in a top perspective view and bottom perspective view, respectively. The rod receiving inlay comprises an elongated inlay body having an inlay top face 78 and an opposite inlay bottom seat or face 72. Throughout the top face, a rod receiving aperture, channel or seat 71 extends lengthwise across the length of the inlay body. The rod receiving aperture has an aperture or channel width AW and an aperture channel length AL, and it is sized and shaped to hold a rod in a substantially play-free manner. In this example, the aperture length (AL) to aperture width (AW) ratio (AL:AW) is at least 1.5:1, and more specifically at least 2:1. Furthermore, in the inlay bottom seat 72, the rod receiving inlay comprises at least one tool clearance or aperture 73a, 73b sized and shaped to provide a space for a bone fastener insertion tool, such as a screwdriver. In one example, as depicted in FIGS. 5A to 5D, the inlay body bottom seat 72 is sized and shaped to mate with the bone fastener engaging insert 50. Alternatively, the bottom seat may be configured to directly engage against the bone fastener 10. Depending on the shape of the bone fastener head, the bottom seat may be flat or cylindrically curved, as explained later with reference to FIGS. 9A to 9F. The inlay further comprises at least one nose or hook 75a, 75b extending or protruding from the side of the inlay. The hook serves the purpose of being a fixation feature sized and shaped to engage with a respective cut-out 35a, 35b of the connector head. When engaged the connection between the hook and the cut-out inhibits unwanted disassembly of the inlay and the connector head 20. It is to be noted that the described functionality of inhibiting unwanted separation can be obtained in many different ways.

Figure 5C:
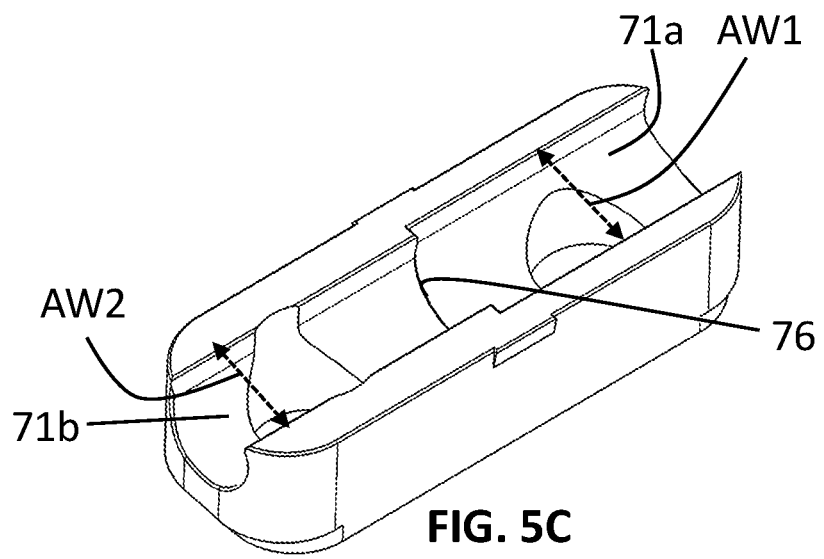
Figure 5D:
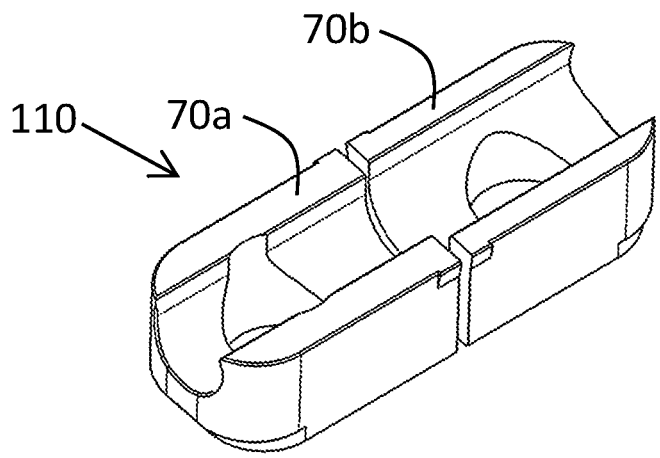

The inlay 70 of FIG. 5C comprises a stepped aperture 71. More specifically, the aperture 71 comprises a first aperture section 71a having a first aperture width AW1, and a second aperture section 71b having a second, different aperture width AW2, meeting in a transition region 76. The different aperture sections are configured for insertion of differently sized rods. FIG. 5D shows an inlay assembly 110 comprising at least a first inlay 70a and a second inlay 70b. Accordingly, the pocket of the elongated connector head may be configured to receive a plurality of rod receiving inlays. The inlays may comprise differently sized apertures 71, namely having a first aperture width AW1 and a second aperture width AW2. By combining specific inlays, the bone fastener assembly 1 can be customised to receive specific rod sizes.

Figure 6A:
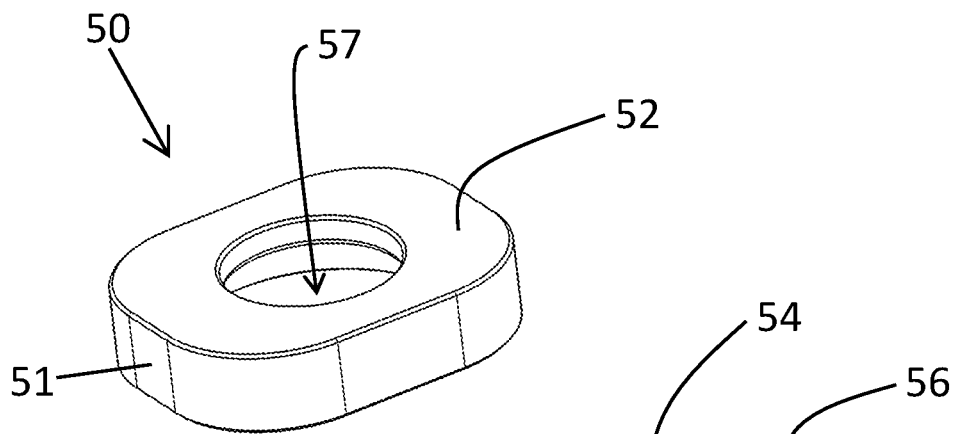
FIGS. 6A and 6B depict a bone fastener engaging insert in detail.
Figure 6B:
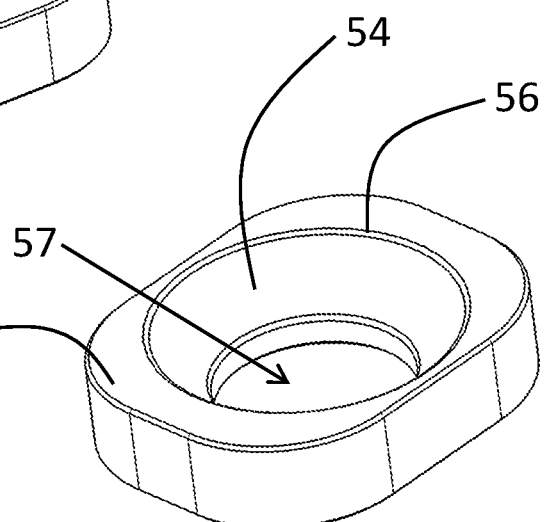

FIGS. 6A and 6B illustrate the bone fastener engaging insert 50, which in this example is a disc-shaped element. The insert 50 comprises an insert body 51, having an insert top side 52 and an insert bottom side 53, including a concave recess 54, also referred to as a bone fastener head engaging recess. The concave recess has at least a partly circular edge 56. As described later, the concave recess is configured to mate with the fastener spherical head in a forceful manner, and inhibit motion of the bone fastener in relation to the insert 50. Friction and holding forces are provided by contact over a larger mating area. In order to be able to screw the bone fastener into a target bone, the insert 50 comprises a central through bore or hole 57, through which a tool, such as a screwdriver, can engage into the drive 17 of the bone fastener. Alternatively, the recess 54 can be shaped in a non-complementary manner to the spherical head, in such a manner, that only the circular edge, or parts of the circular edge engage against the bone fastener head. Friction and holding forces are provided by means of a line or point contact. The insert and recess may be sized and shaped to engage against the top half 18 and/or bottom half 19 of the bone fastener. In this example, the insert is, as shown in FIGS. 2A and 2B, sized and shaped to engage against the top half 19 of the spherical head 15.

Figure 7A:
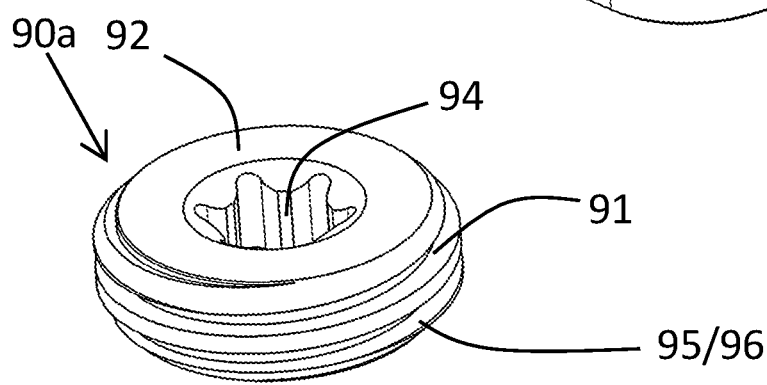
FIGS. 7A and 7B depict the rod fastener in detail.
Figure 7B:
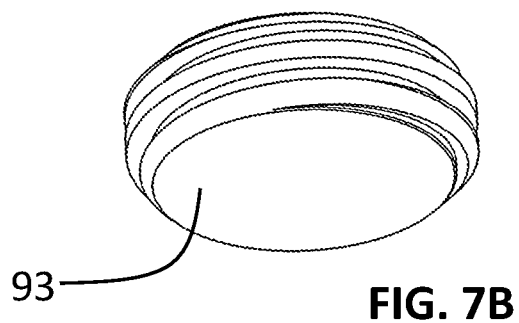

FIGS. 7A and 7B illustrate one of the rod fasteners 90a in greater detail. The rod fastener 90a comprises a rod fastener body 91 having a rod fastener top side 92 and a rod fastener bottom side 93. A rod fastener drive 94 extends into the body and is intended to engage with a locking tool, such as a screwdriver, providing a means to lock the rod fastener into the elongated connector head. In this example, the rod fastener comprises an external locking means 95, which is shaped as an external thread 96. Furthermore, in this example, the rod fastener bottom side 93 is flat, and configured to engage against a posterior rod 100, 101.

Figure 8A:
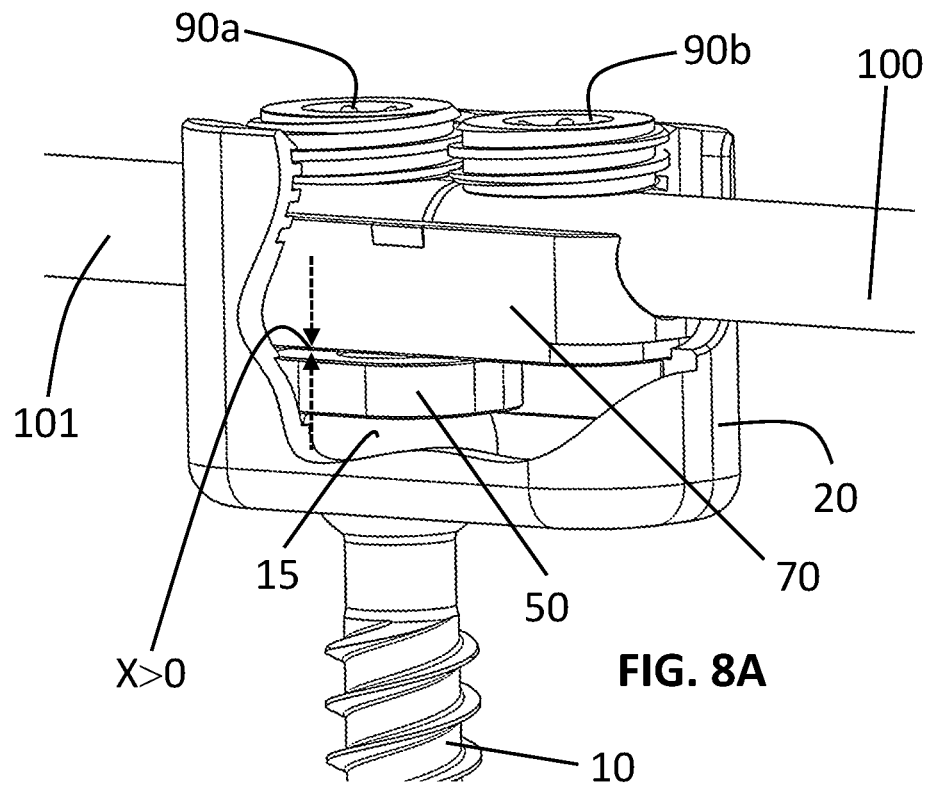
FIGS. 8A and 8B depict the interaction of the individual components of the bone fastener assembly in detail.
Figure 8B:
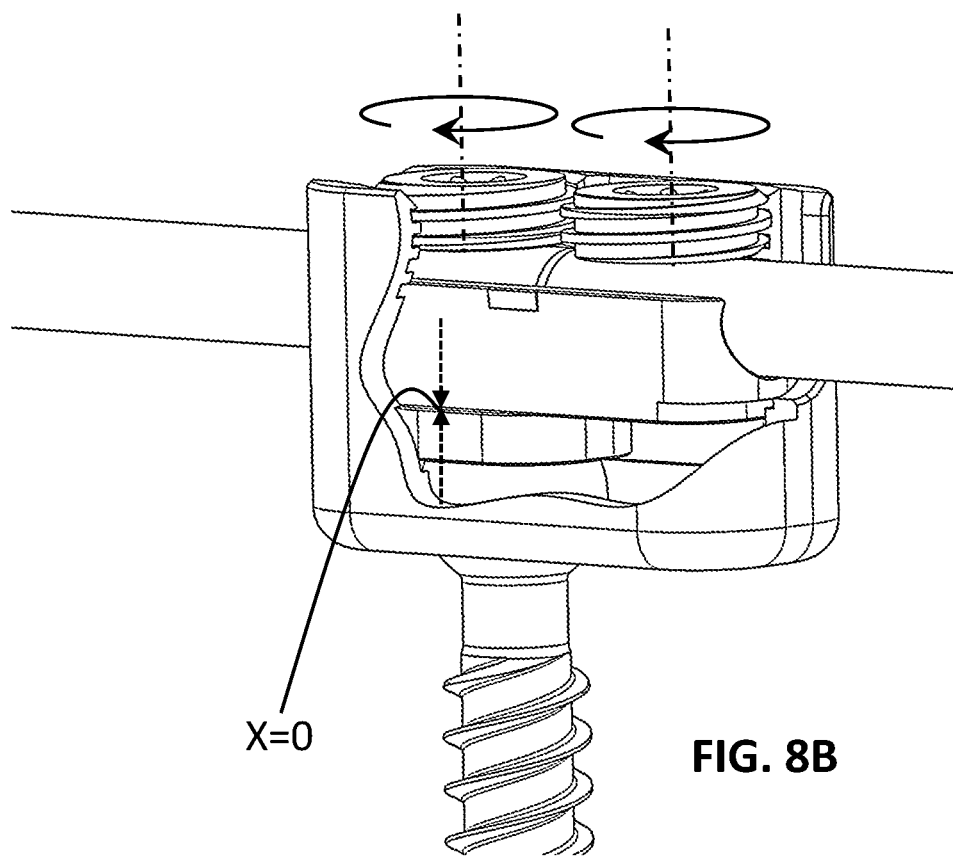
Figures 9A, 9B:
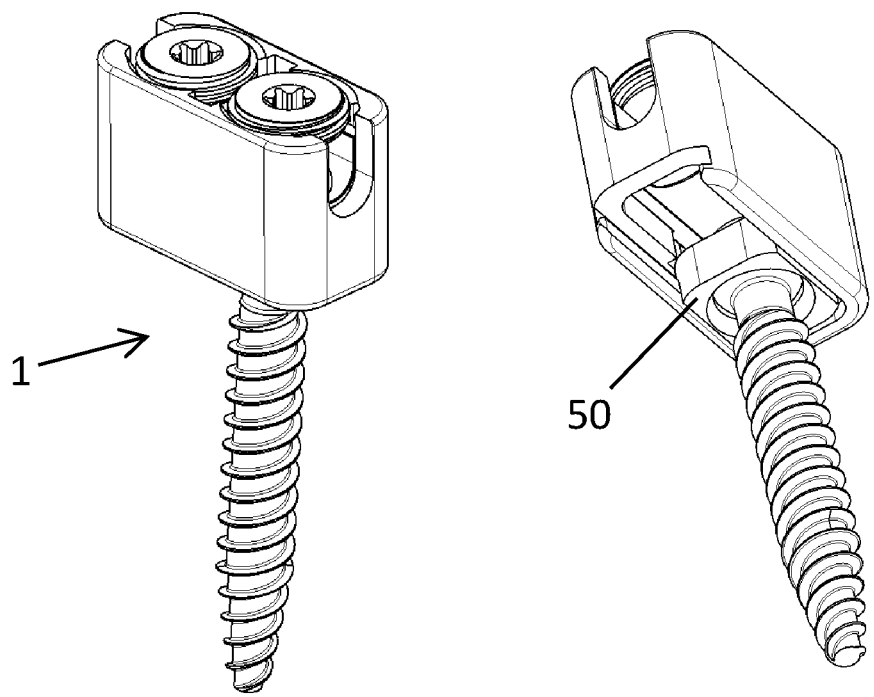
FIGS. 9a to 9F depict an alternative design of the bone fastener assembly in detail.
Figure 9C:
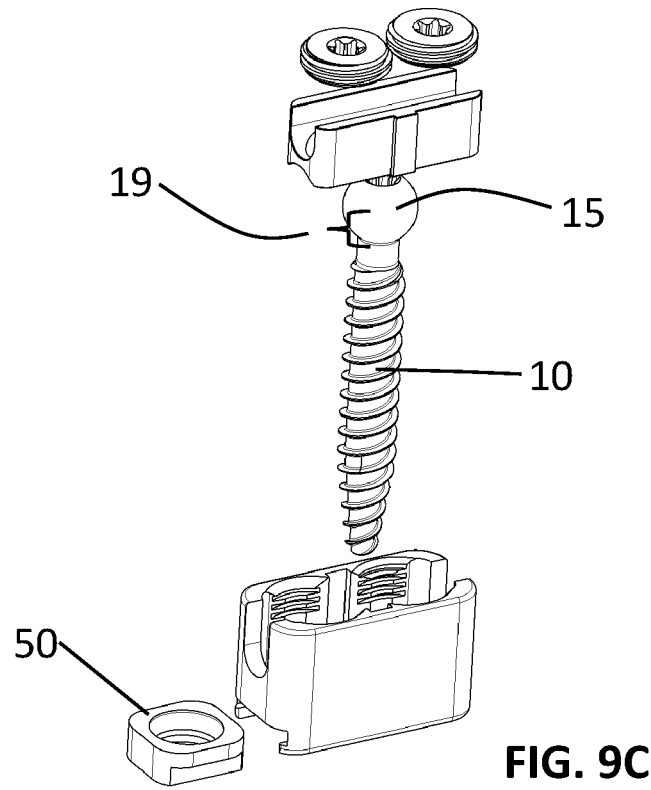
Figure 9D:
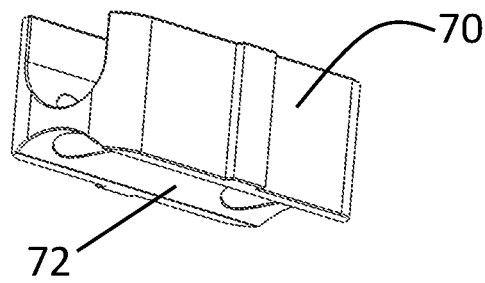
Figure 9E:
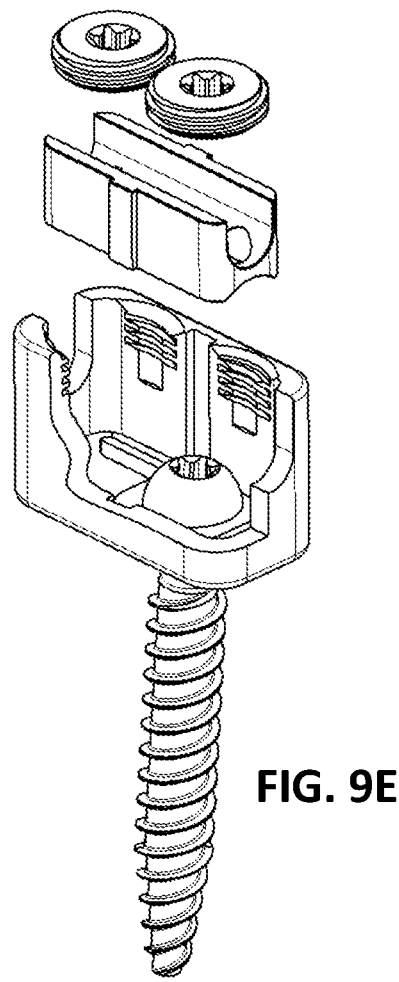
Figure 9F:
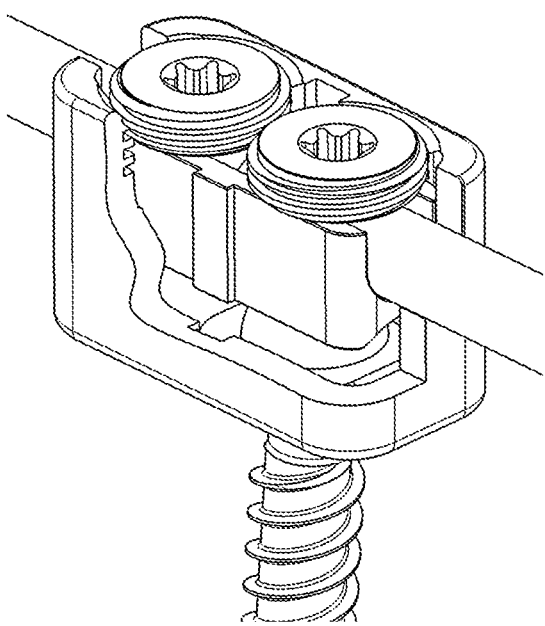

FIGS. 8A and 8B illustrate the locking principle of the bone fastener assembly. Upon tightening of the respective rod fastener 90a, 90b, which is threadedly engaged in the connector head 20, the rod fastener presses against the respective rod 100, 101, which is pressed against the inlay 70, which is in turn pressed against the insert 50, which is then pressed against the bone fastener 10 or more specifically the spherical head 15, which is mating against the channel bottom portion 47, and therefore is pressed against the elongated connector head. Thus, upon tightening, all the elements of the assembly will block each other's ability to move. The play X between the parts, which allows the parts to move in relation to each other is decreased to zero.

FIGS. 9A to 9F show an alternative design of the bone fastener assembly 1. In this design, the insert 50 is sized and shaped to engage against the bottom half 19 of the spherical head 15 of the bone fastener 10. Furthermore, the inlay 70 comprises a bottom seat 72, which is sized and shaped to engage against the top half 18 of the spherical head 15 of the bone fastener 10, and providing holding forces and friction by means of a line contact. Therefore, in this example, the bottom seat is configured as a half cylindrical space or shape. In the present example, the rigid fixation of the bone fastener assembly, including the placed rods 100, 101, is achieved by tightening the respective rod fastener 90a, 90b (which is engaged with the respective locking means 32a, 32b of the elongated connector head 20), which presses against the respective rod 100, 101, which presses against the inlay 70, which presses against the bone fastener spherical head 15, which presses against the insert 50, which presses against the elongated head. Thus, all the elements of the assembly block each other's ability to move.

FIGS. 10A to 10D show a further alternative design of the bone fastener assembly 1. In this example, the elongated connector head 20 has a curved or bent shape to receive the inlay 70, which is sized and shaped to receive two rods that are oriented in a non-parallel manner. In this example, the shape is curved in a plane, which is parallel to the longitudinal axis of the bone fastener 10. In order to receive these non-parallel rods, the inlay 70 comprises at least two apertures, namely first and second aperture sections 71a, 71b having first and second aperture axes AA1, AA2, respectively, at an obtuse angle.

FIGS. 11A to 11C show yet another design of the bone fastener assembly 1. In this example, at least two passages 27a, 27b extend between the first head side 23 and the second head side 24, thus extending sideways over the elongated connector head width. In this case, the rod receiving inlay 70 comprises at least two apertures 71a, 71b, so that a first aperture 71a is aligned with a first passage 27a, while a second aperture 71b is aligned with a second passage 27b. The inlay may comprise differently sized apertures 71a, 71b, namely having a first aperture width AW1 and a second, different aperture width AW2.

Figure 12A:
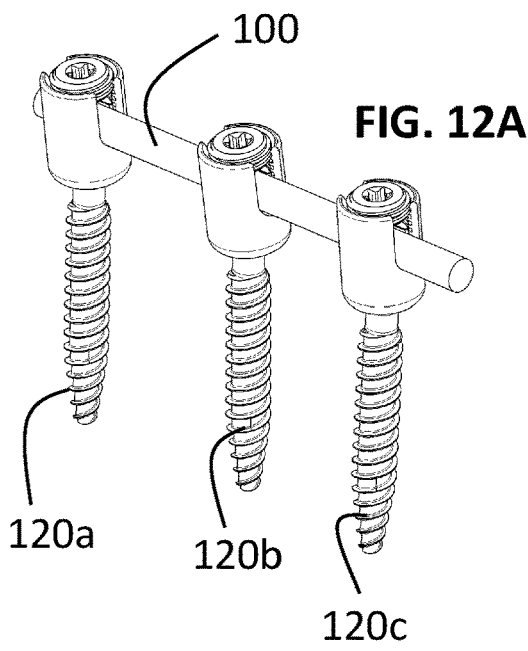
FIGS. 12A to 12N depict one example surgical procedure, where a construct is elongated.
Figure 12B:
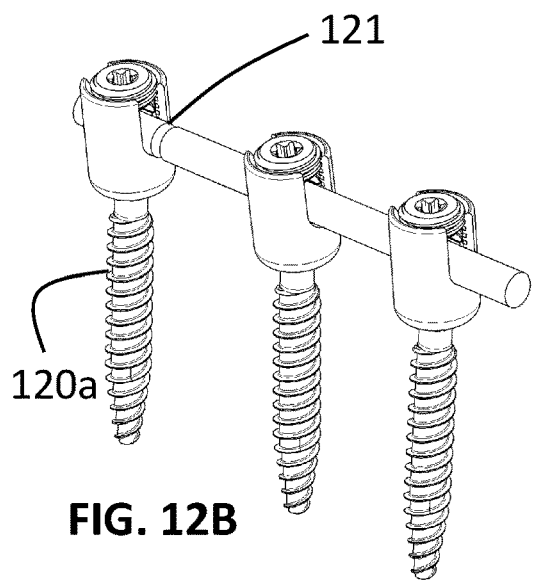
Figure 12C:
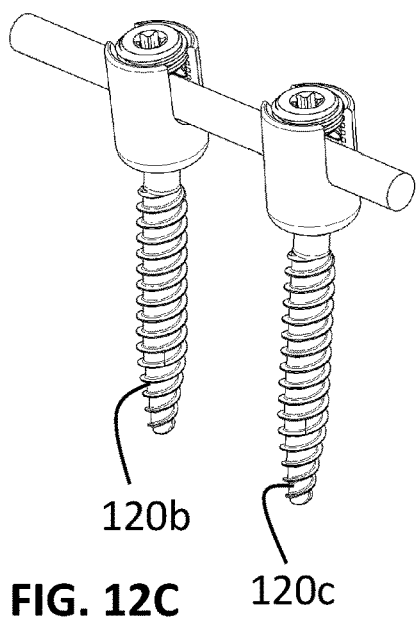
Figure 12D:
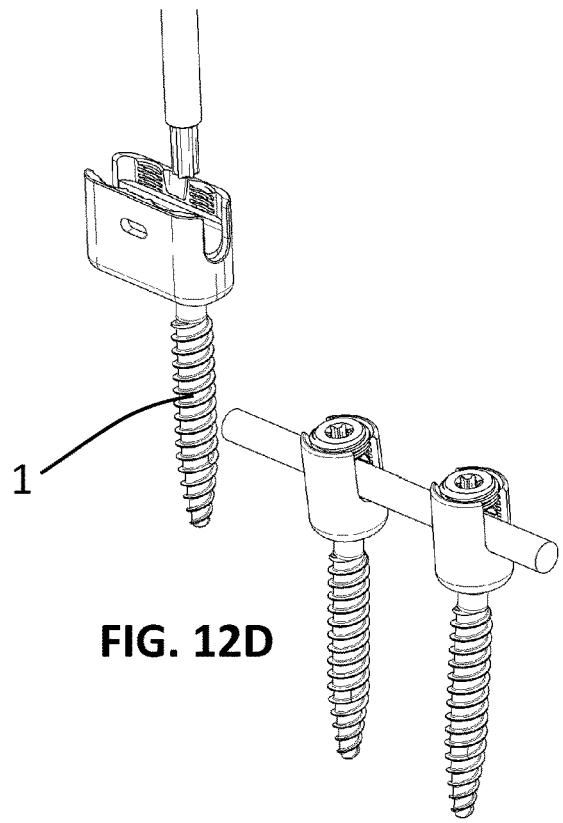
Figure 12E:
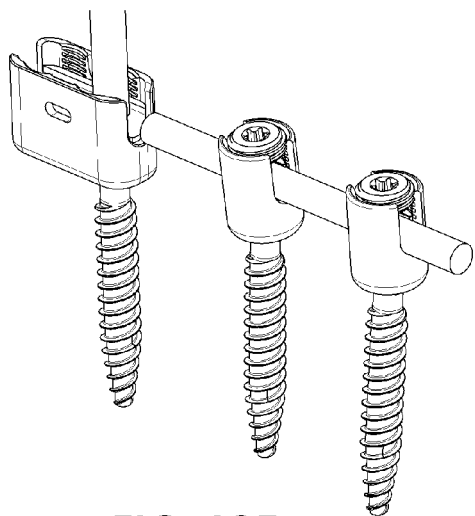
Figure 12F:
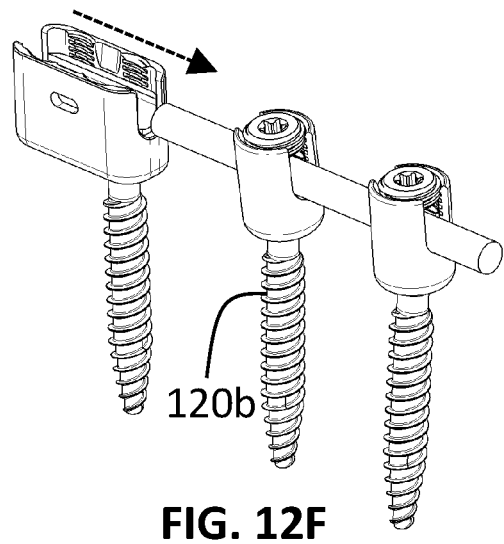
Figure 12G:
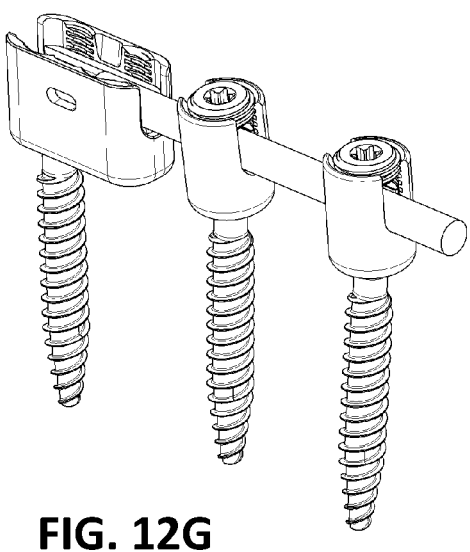
Figure 12H:
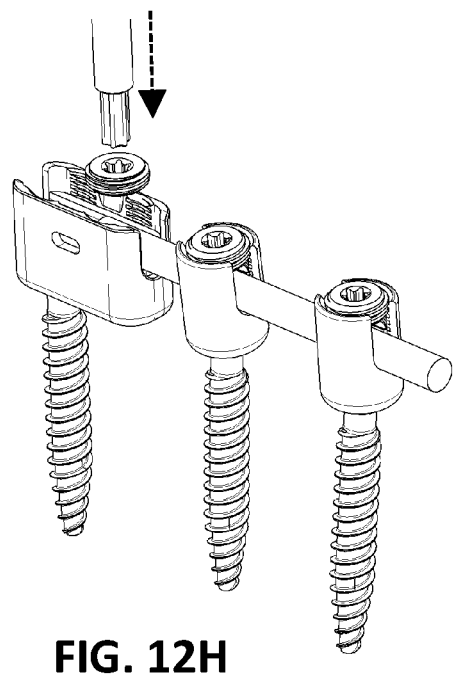
Figure 12L:
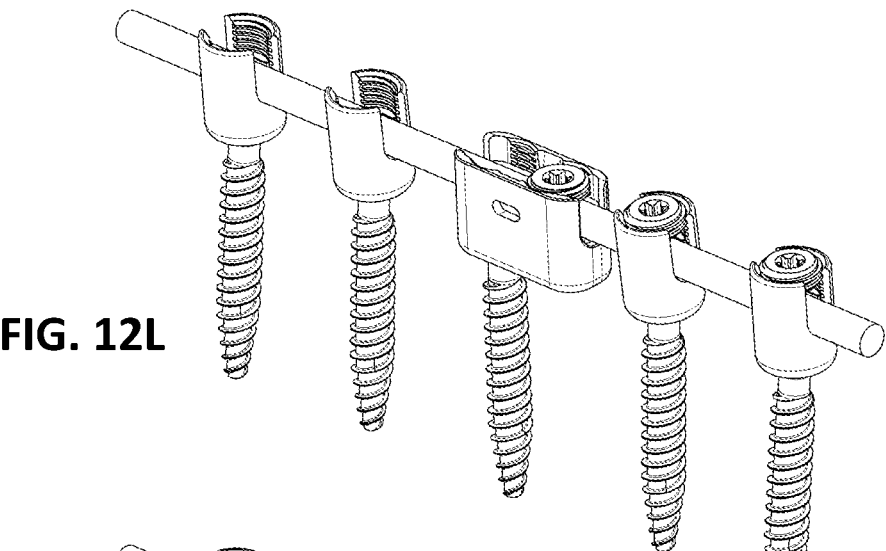
Figure 12M:
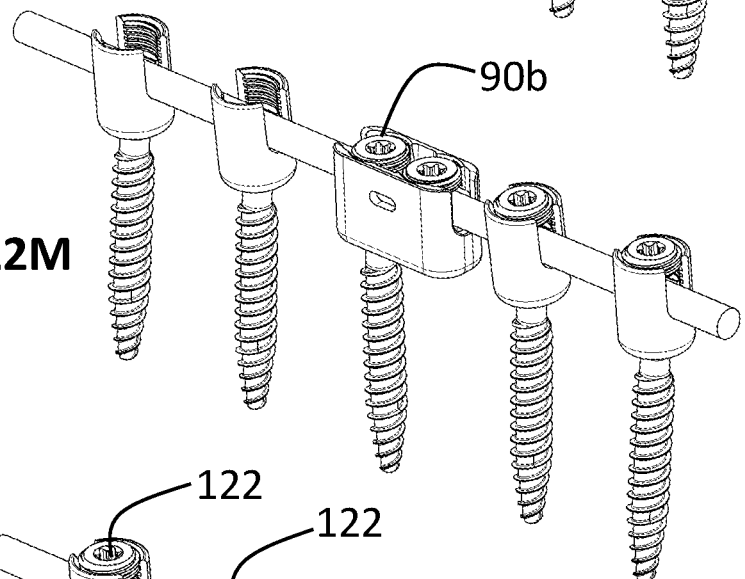
Figure 12N:
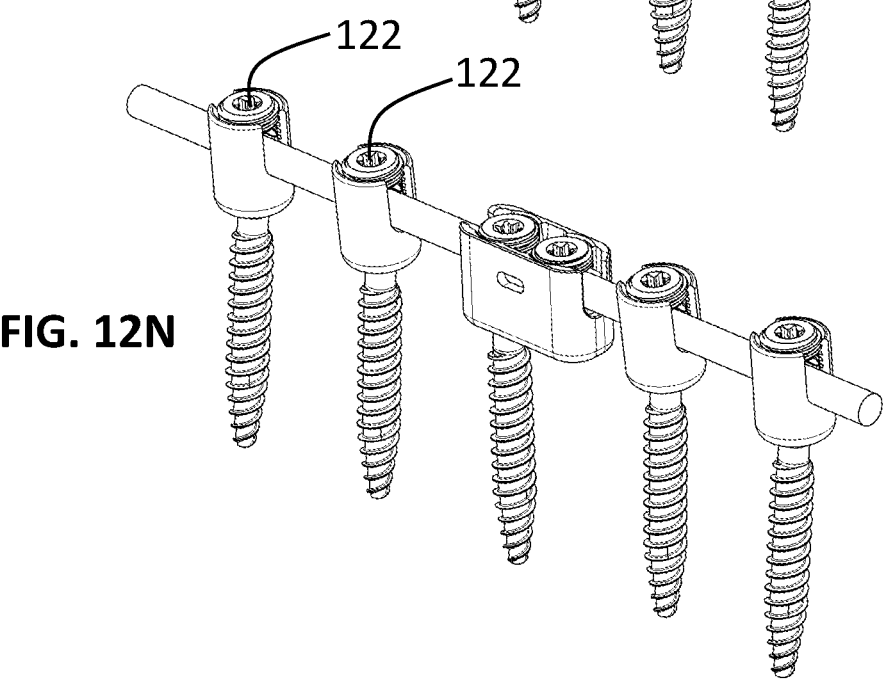

FIGS. 12A to 12N illustrate an example surgical technique or procedure for elongating an existing posterior stabilisation construct. For illustration purposes, no bony structures are shown. FIG. 12A depicts an implanted, in situ posterior spinal stabilisation construct, including first, second and third state-of-the-art pedicle screws 120a, 120b, 120c, which are connected by a rod 100. In this illustrative example, the first pedicle screw 120a has loosened at the bone-screw interface and needs to be removed. For restabilising the spine, the first pedicle screw 120a needs to be replaced, and the construct needs to be extended to at least one next vertebral level. FIG. 12B depicts the cut-off 121 near the loosened pedicle screw 120a. By using a grinding tool, the rod is cut. FIG. 12C depicts the posterior construct after removal of the loose pedicle screw 120a. FIGS. 12D and 12E depict the insertion of the bone fastener assembly 1 into the target bone at the location of the removed pedicle screw 120a. FIGS. 12F and 12G depict the sliding step of the elongated connector head 20 towards the second pedicle screw 120b so that a portion of the elongated connector head 20 is placed under the cut-off rod 100. FIGS. 12H and 12I depict the placement of a first rod fastener 90a to fixate the rod 100 into the elongated connector head 20. FIG. 12J depicts the extension of the posterior construct to further two vertebral levels, by using fourth and fifth state-of-the-art pedicle screws 120d and 120e. FIGS. 12K and 12L depict the insertion of a second rod 101, and the engagement of the second rod 101 with the bone fastener assembly 1 and with the fourth and fifth pedicle screws 120d, 120e. FIGS. 12M and 12N depict the placement of the rod fastener 90a and two set screws 122 to rigidly fixate the extended construct.

Figure 13A:
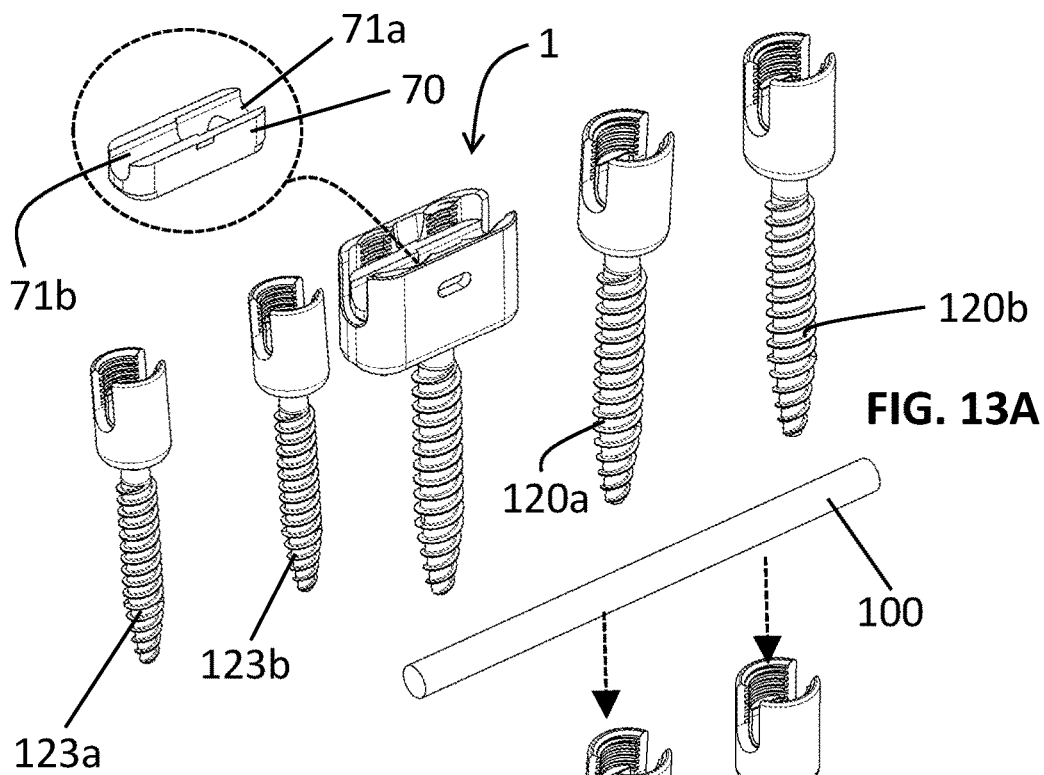
FIGS. 13A to 13G depict one example surgical procedure, where a primary construct is placed.
Figure 13B:
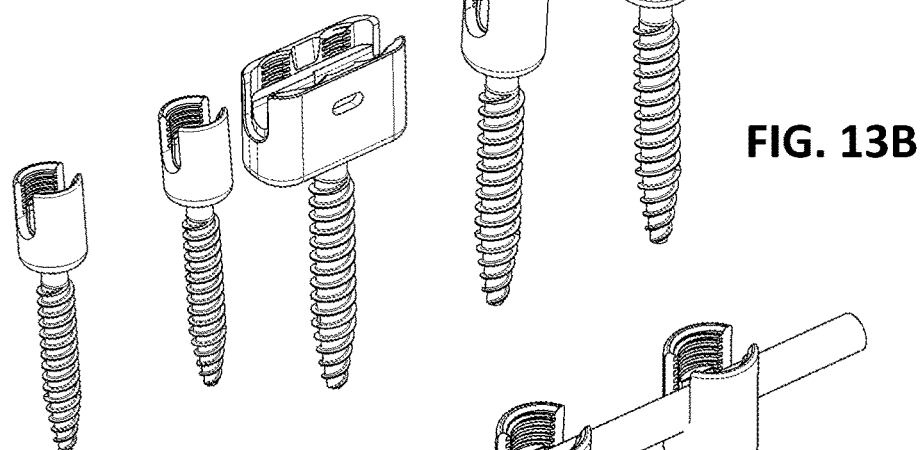
Figure 13C:
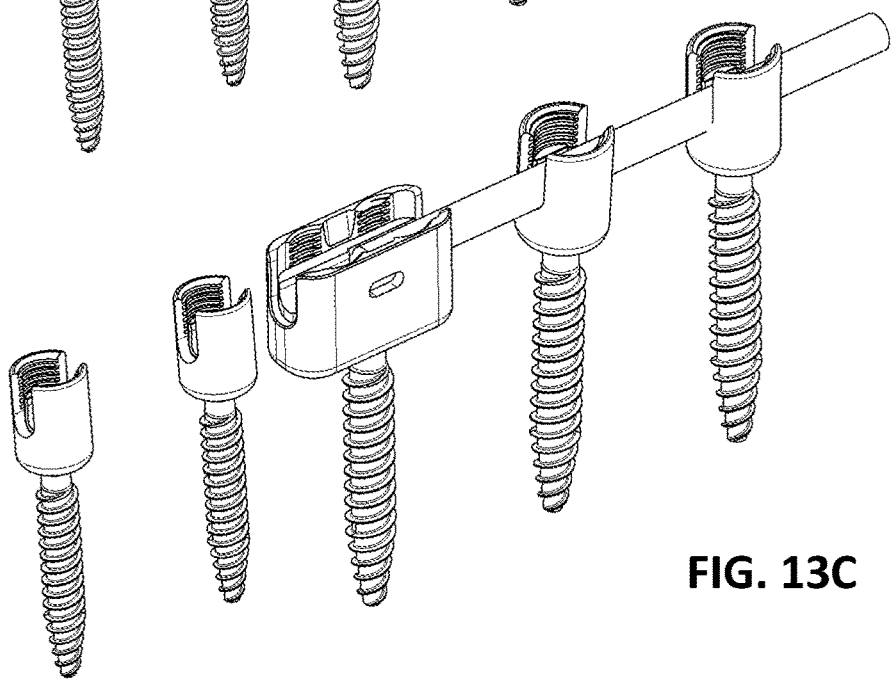
Figure 13D:
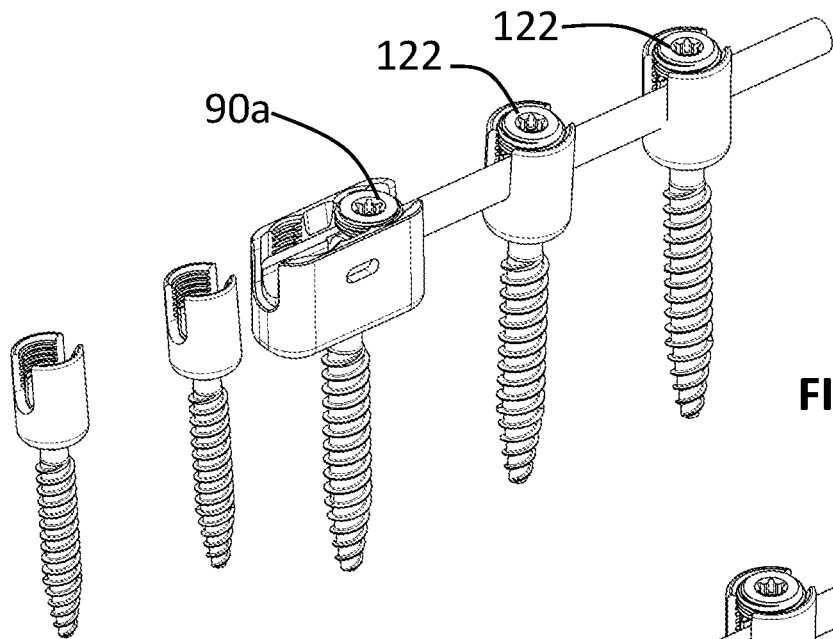
Figure 13E:
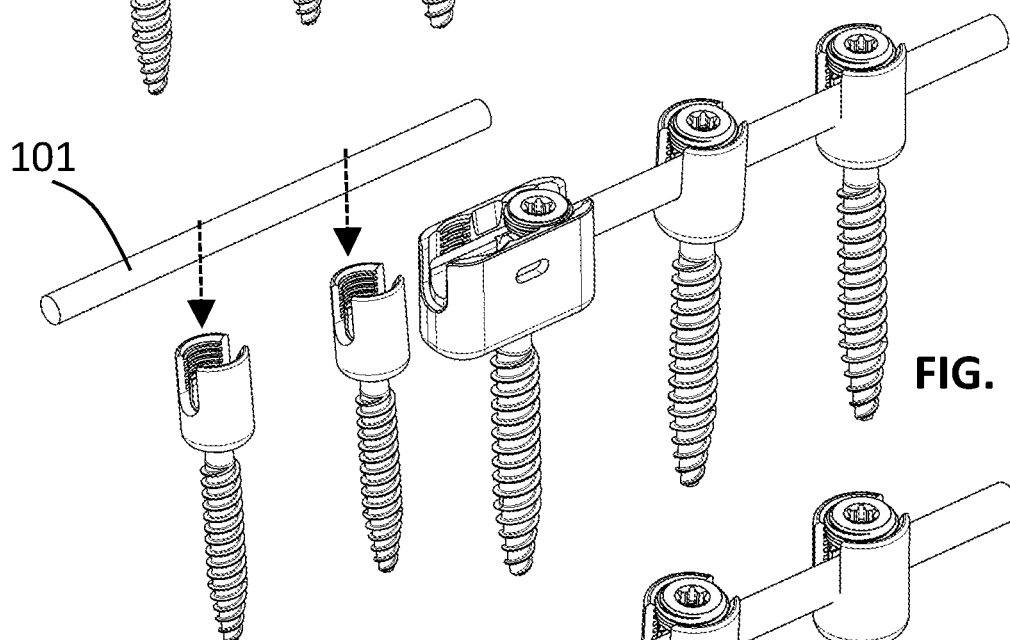
Figure 13F:
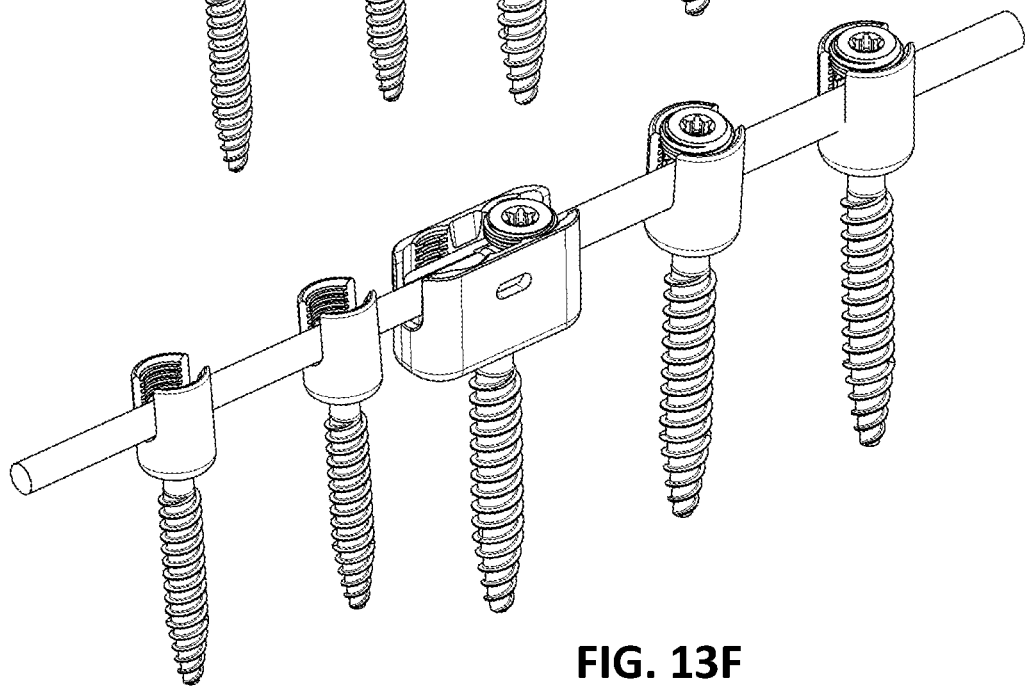
Figure 13G:
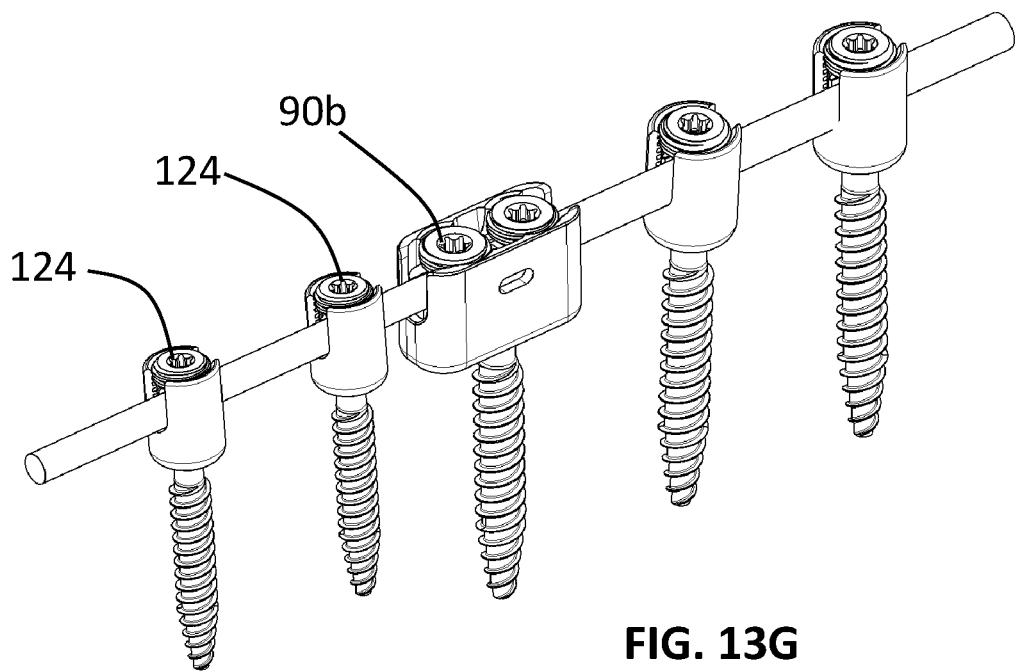

FIGS. 13A to 13F illustrate an example surgical technique or procedure for placing a new posterior stabilisation construct. For illustration purposes, no bony structures are shown. In this example, a posterior stabilisation construct is placed that requires a transition from a thicker rod to a smaller rod diameter. FIG. 13A depicts two large state-of-the-art pedicle screws 120a, 120b, the bone fastener assembly 1, and two smaller state of the art pedicle screws 123a, 123b. In this example, a transition of a large rod and large screws to a smaller rod and smaller screws in the middle of the construct is required. Moreover, the inlay 70 is depicted, comprising a stepped aperture 71. The aperture 71 comprises a first aperture section 71a having a first aperture width AW1 and a second aperture section 71b having a second, different aperture width AW2, meeting in a transition region 76. The aperture sections are configured for insertion of differently sized rods. FIGS. 13B and 13C depict a large posterior rod 100 being placed into heads of the large pedicle screws 120a and 120b, and into the elongated connector head 20 of the bone fastener assembly 1. The rod is engaged in the larger aperture 71a of the inlay 70. FIG. 13D depicts the placement of the rod fastener 90a and two set screws 122 to rigidly fixate the larger rod 100. FIGS. 13E and 13F depict the step of a smaller posterior rod 101 being placed into heads of the smaller pedicle screws 123a, 123b, and into the elongated connector head 20 of the bone fastener assembly 1. The rod is engaged in the smaller aperture 71b of the inlay 70. FIG. 13G depicts the placement of the rod fastener 90b and two set screws 124 to rigidly fixate the smaller rod 101.

Figure 14A:
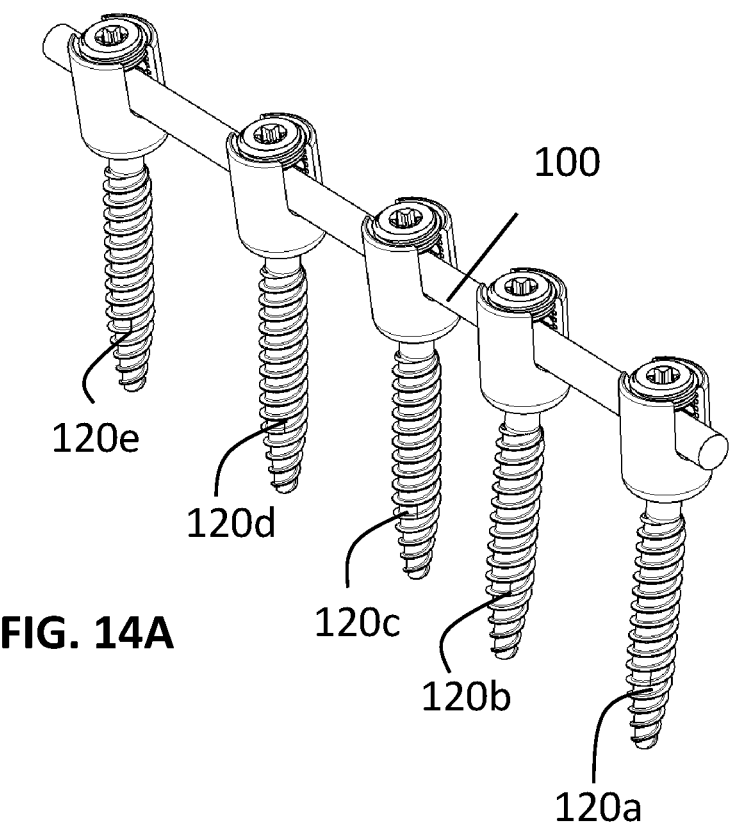
FIGS. 14A to 14E depict application scenarios of the bone fastener assembly, where a loose screw in the middle of a construct is replaced.
Figure 14B:
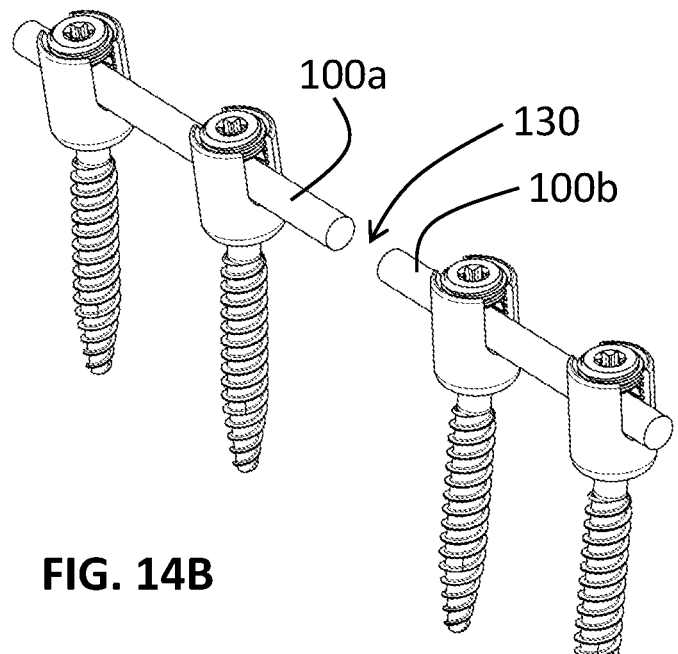
Figure 14C:
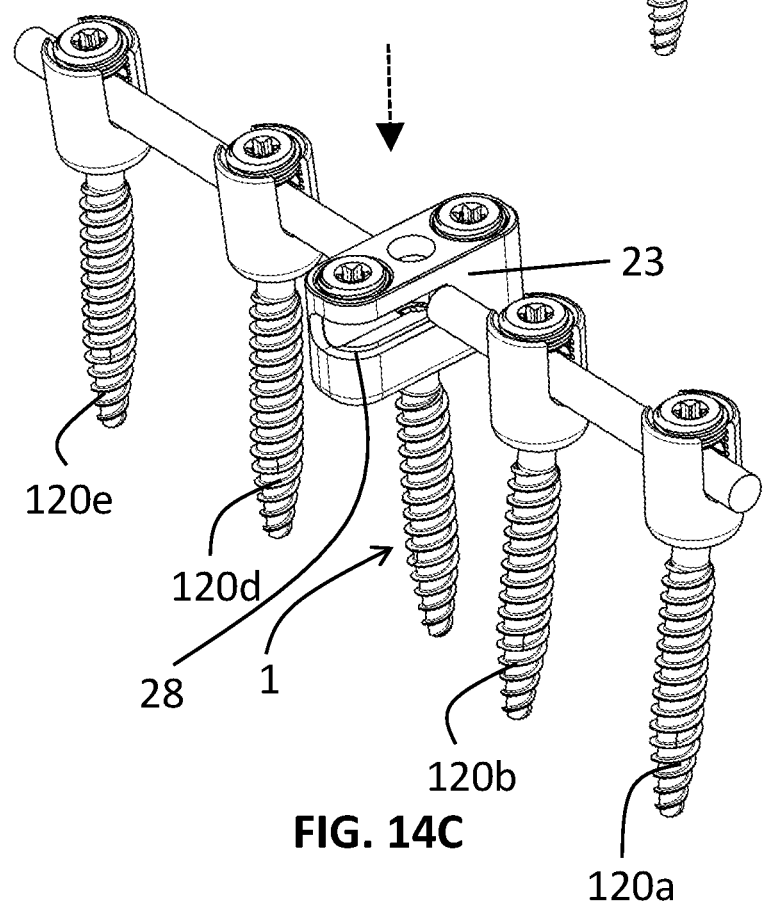
Figure 14D:
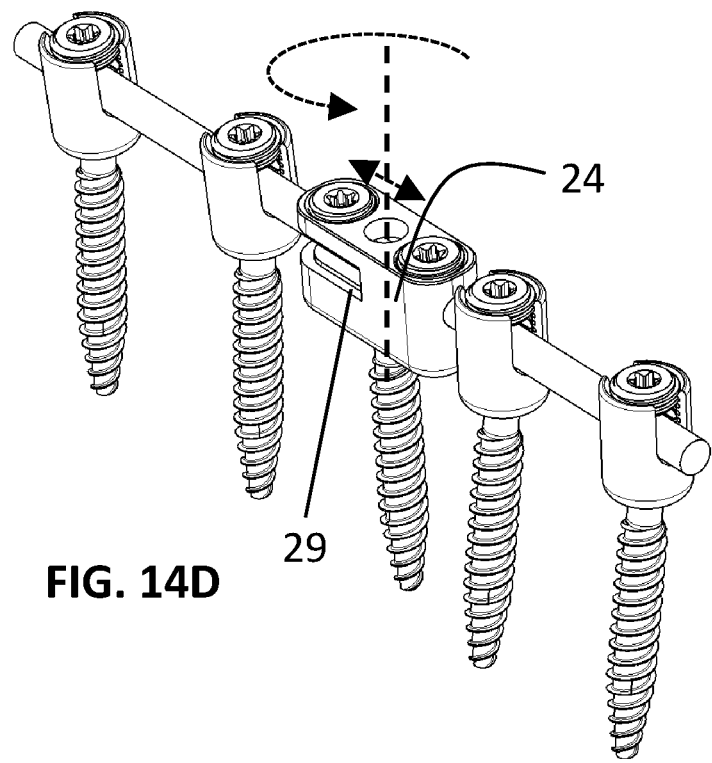
Figure 14E:
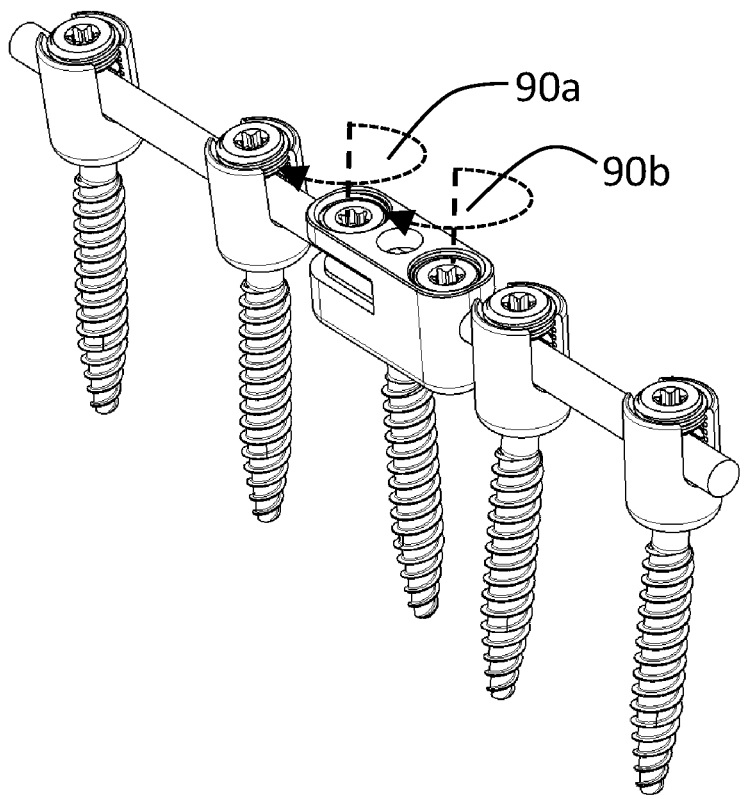

FIGS. 14A to 14E depict application scenarios to replace a loosened bone fastener or pedicle screw in the middle of a construct in a minimally invasive manner. FIG. 14A depicts a construct including five pedicle screws 120a, 120b, 120c, 120d, 120e, wherein the third pedicle screw 120c has loosened. FIG. 14B depicts the removal of the third pedicle screw. The rod 100 has been cut very near to the head of the third pedicle screw 120d. The third pedicle screw and a small rod fragment has been removed, leaving two rod halves 100a, 100b in place and a gap 130 between them. FIG. 14C depicts the placement of the bone fastener assembly 1 into the gap 130. FIG. 14D depicts the rotation and sliding of the elongated connector head 20 of the bone fastener assembly 1 to engage the elongated connector head 20 over the two rod halves 100a, 100b. The rod halves are received within the passage 27. In this example, the passage comprises a passage start section 28 and a passage end section 29, where the passage start section is open to the first head side 23 and the passage end section is open to the second head side 24, or vice versa. In other words, the passage start section 28 forms a slot, which in this example is a longitudinal slot, in the first side wall of the connector head 20, while the passage end section 29 forms a second slot, which in this example is also a longitudinal slot, in the connector head second side wall, or vice versa. In this example, the slots extend parallel or substantially parallel to the longitudinal axis of the connector head 20. FIG. 14E depicts the tightening of the rod fasteners, thereby rigidly fixating the construct.

Figure 15A:
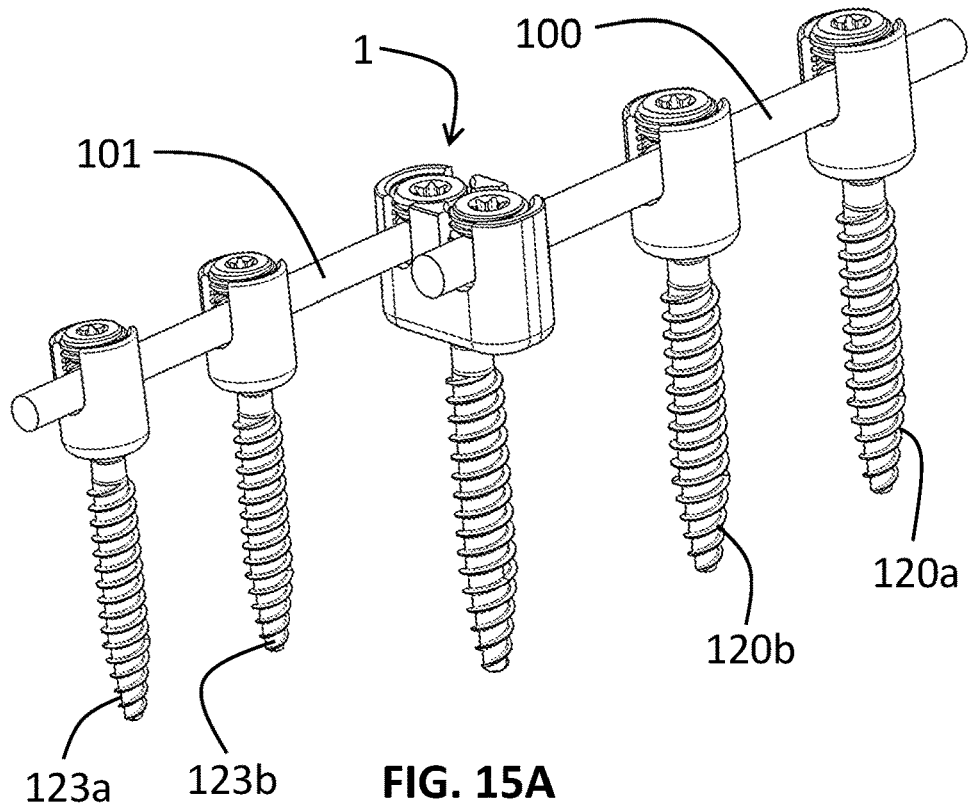
FIGS. 15A and 15B depict an application scenario of the bone fastener assembly of FIGS. 10A to 10D.
Figure 15B:
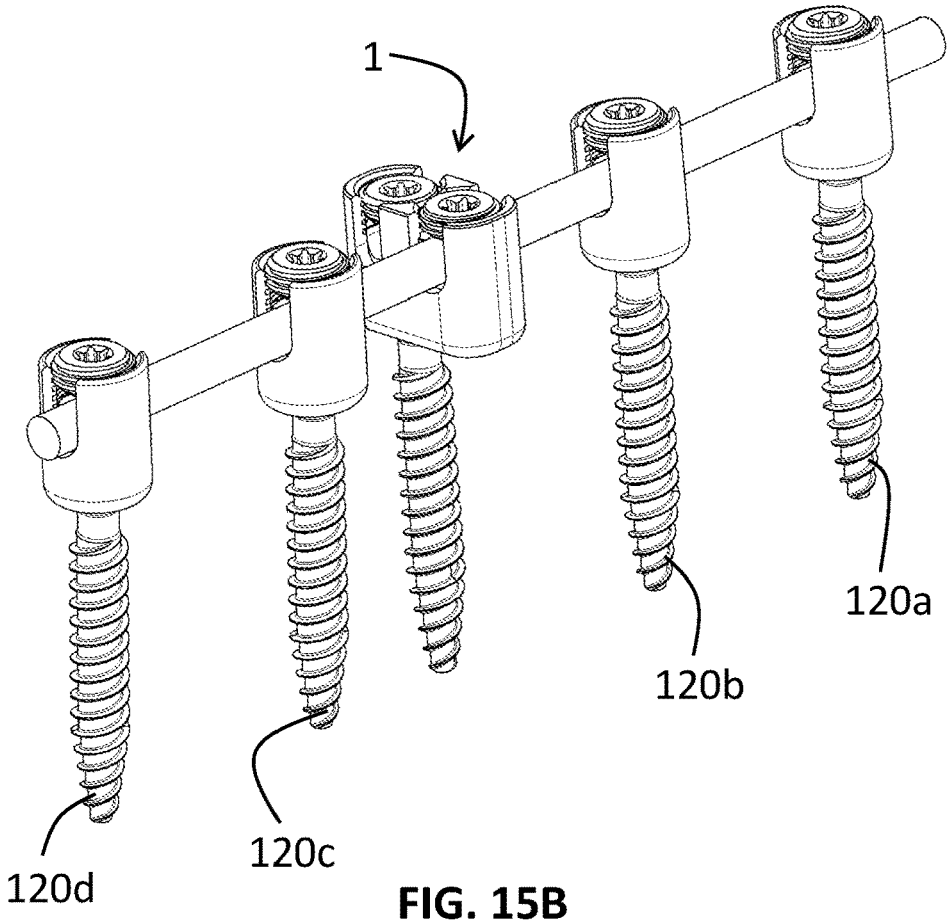

FIGS. 15A and 15B depict two application scenarios of the bone fastener assembly shown in FIGS. 11A to 11C. FIG. 15A depicts a parallel extension, where a thicker rod 100 and a thinner rod 101 are combined in a parallel configuration. FIG. 15B depicts a clinical situation, where one bone fastener has to be placed out of line (formed by the rod) due to the patient individual anatomy. By translating the elongated connector head, in this example orthogonally, or substantially orthogonally to the longitudinal rod axis, the bone fastener assembly can be adapted to the situation, and a normal substantially straight or substantially continuously curved rod can be connected or coupled to the bone fastener assembly 1 and pedicle screws.

Figure 16A:
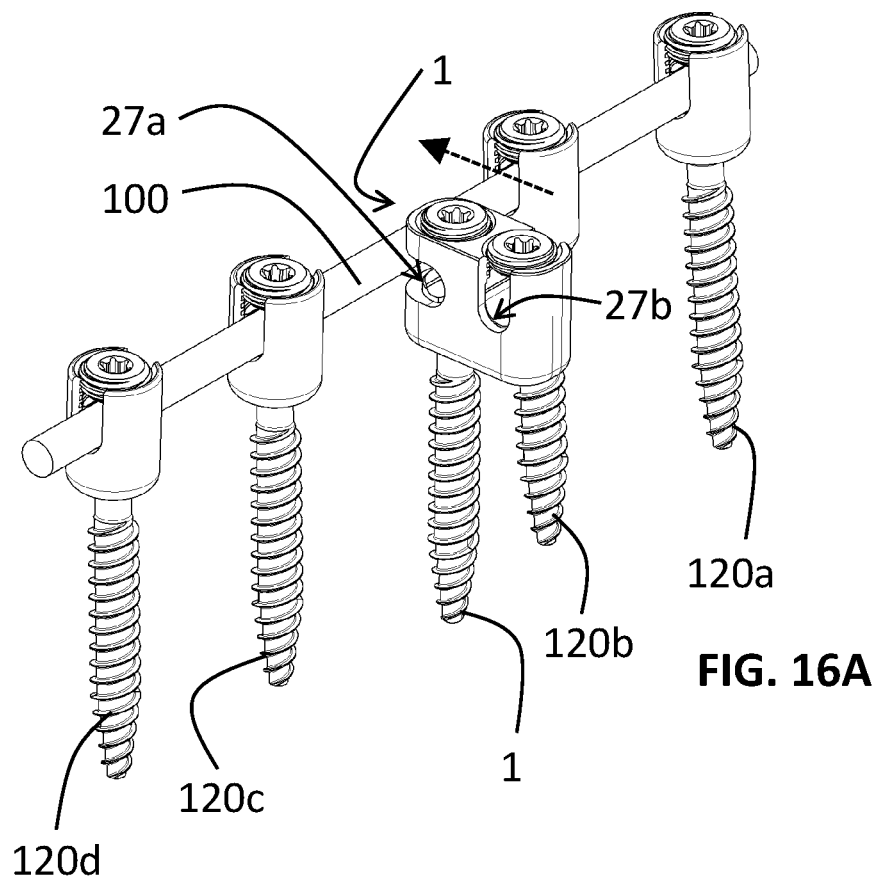
FIGS. 16A and 16B depict an application scenario of a bone fastener assembly, where the rod fastener can receive a rod from the side.
Figure 16B:
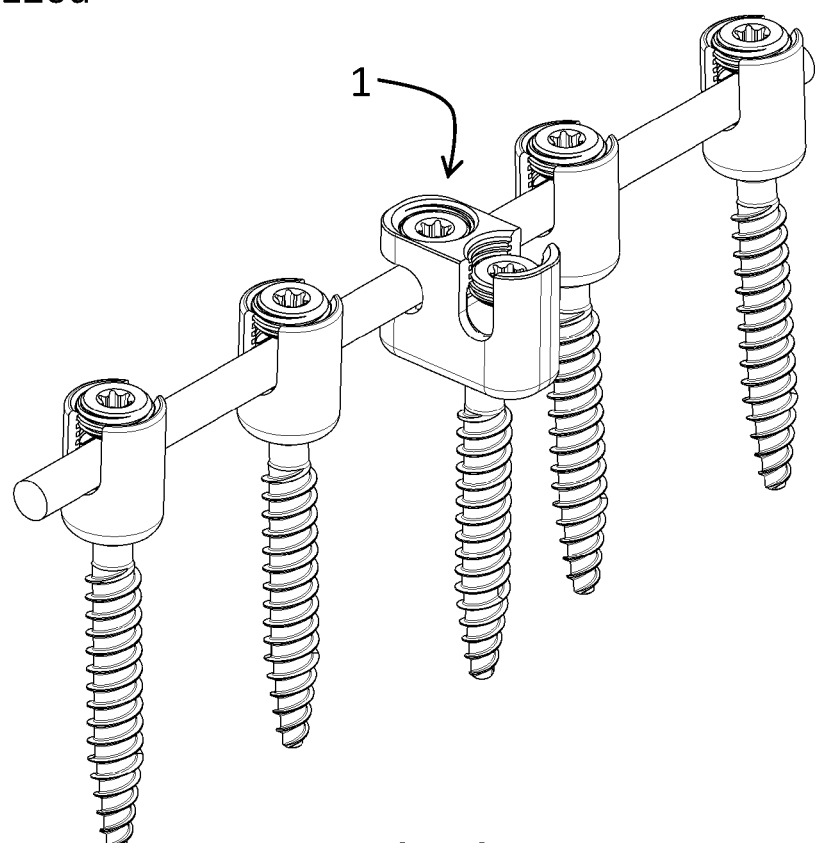

FIGS. 16A and 16B depict an application scenario of a variant of the bone fastener assembly shown in FIGS. 11A to 11C. In this example, the bone fastener assembly, and more specifically the elongated connector head 20, comprises at least one first rod receiving passage 27a, which extends into either the first or second head end 21, 22. In the present example, the elongated connector head also comprises a second rod receiving passage 27b which extends into the head top side 25. As depicted, the horizontally directed or oriented passage allows the elongated head to be slid sideways over the rod. In a second step the rod is rigidly fixated by tightening a rod fastener.

FIG. 16B depicts a clinical situation, where one bone fastener has to be placed out of line due to the patient individual anatomy. By translating the elongated connector head 20, in this example orthogonally, or substantially orthogonally to the longitudinal rod axis, the bone fastener assembly 1 can be adapted to the situation, and a normal substantially straight or substantially continuously curved rod can be connected or coupled to the bone fastener assembly and pedicle screws.

Figures 17A, 17B:
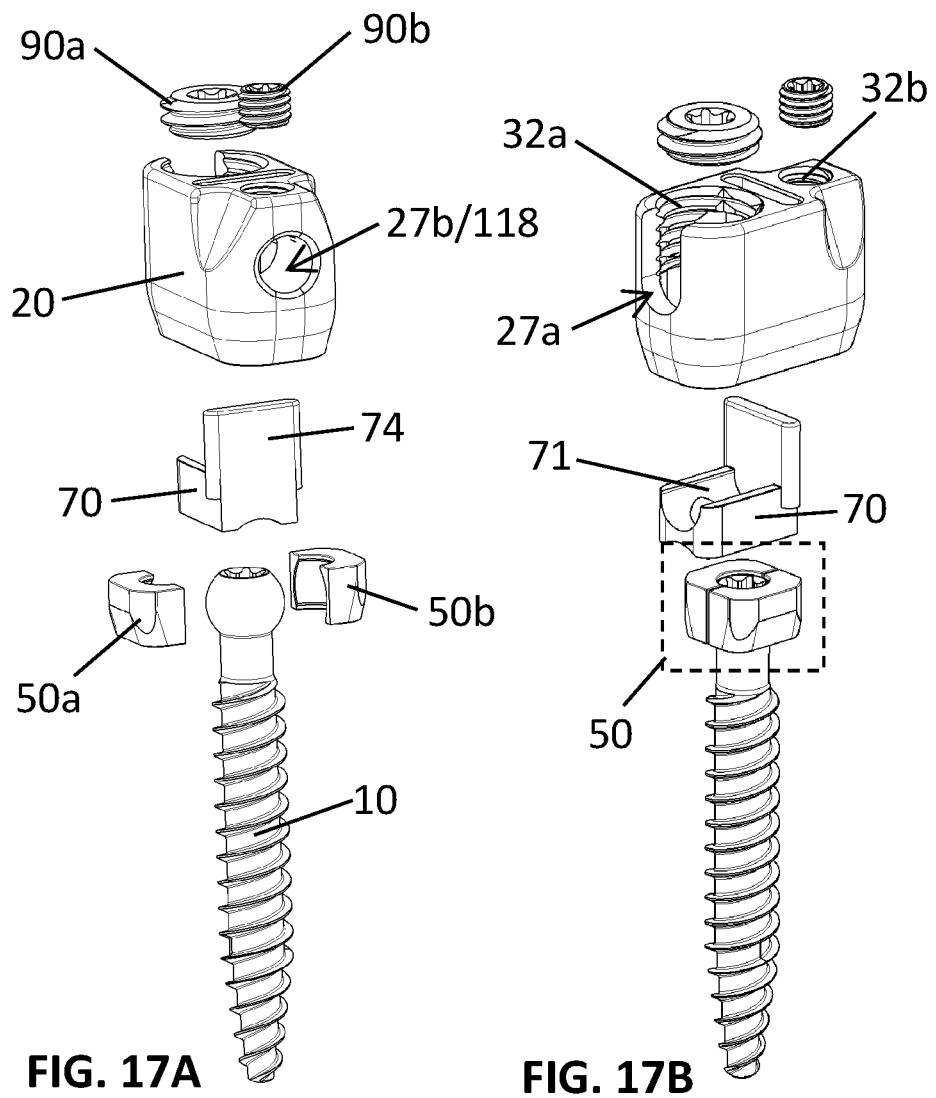
FIGS. 17A to 17D depict yet another design of the bone fastener assembly in detail.
Figure 17C:
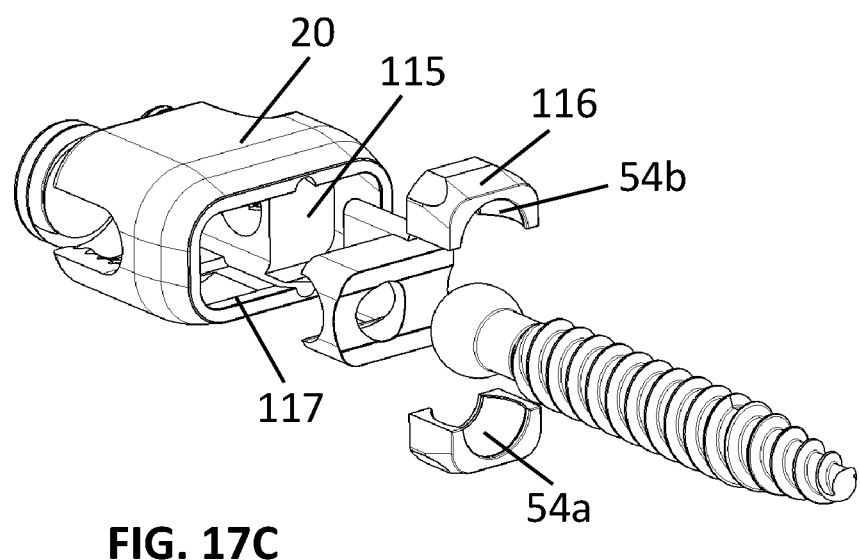
Figure 17D:
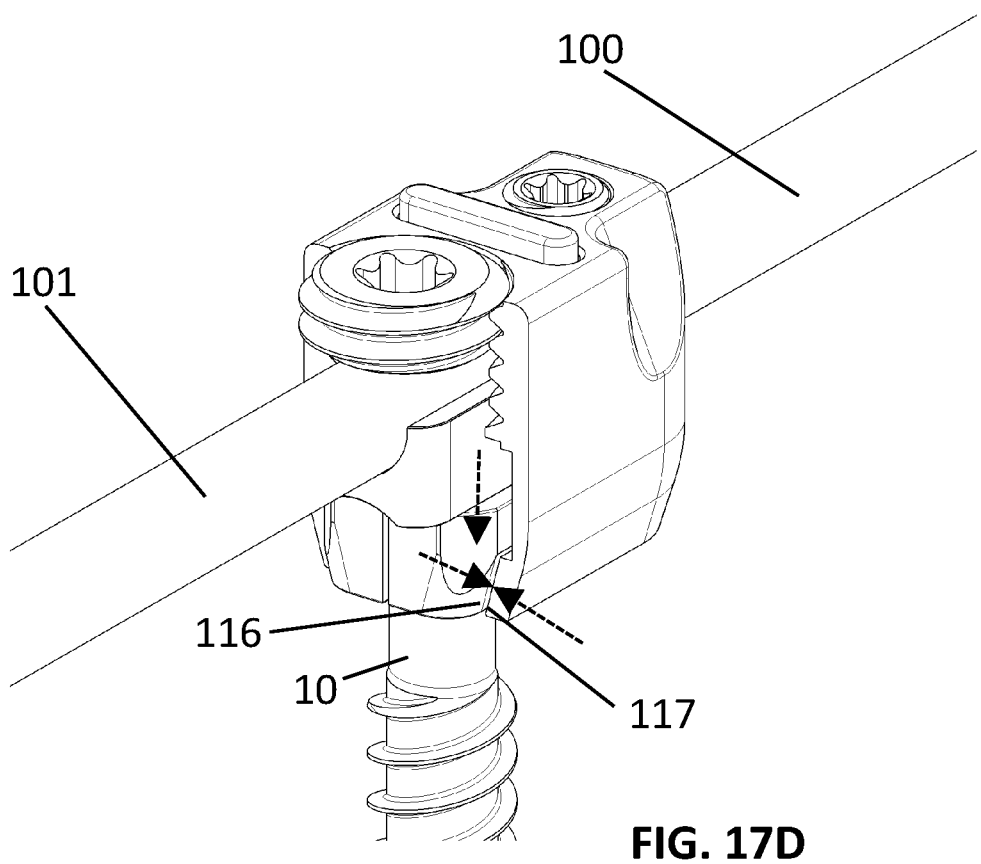

FIGS. 17A to 17D show an alternative design of the bone fastener assembly 1. In this design, the insert 50 comprises a first insert portion or a first insert half 50a and a second insert portion or a second insert half 50b, which are sized and shaped to engage around or at least partially encompass the spherical head 15 of the bone fastener 10. The first insert half and the second insert half comprise a first and second socket 54a, 54b, respectively, which are configured to engage with the spherical head 15 of the bone fastener. Furthermore, the inlay 70 comprises a bottom seat 72, which is sized and shaped to simultaneously engage against the first and second insert portions 50a, 50b, and which provides holding forces. Furthermore, the insert portions comprise a first tapered face 116. The tapered faces 116 are configured to engage with a second tapered face 117 of the elongated connector head 20. As depicted in FIG. 17D, in the present example, rigid fixation of the bone fastener assembly, including the placed rods 100, 101, is achieved by tightening the respective rod fastener 90a, 90b (which is engaged with the respective locking means 32a, 32b of the elongated connector head 20), which presses against the respective rod 100, 101, which presses against the inlay 70, which in turn presses against the insert portions 50a and 50b, which are then forced inwards by the mating first and second tapered faces 116, 117, and so clamp the spherical head 15 of the bone fastener. The mating first and second tapered faces 116, 117 inhibit motion between the insert portions and the elongated connector head. Thus, all the elements of the assembly block each other's ability to move.

The elongated connector head of the design of FIGS. 17A to 17D comprises a shortened inlay 70 having only one rod receiving aperture or channel 71, which overlaps or coincides with the first rod receiving passage portion 27a. On the opposite side, a second rod receiving passage portion 27b is shaped as an opening or a bore 118, i.e. a closed channel. In this example, the bore 118 is sized and shaped to encompass the rod 100 in a substantially play-free manner. The first and second passage portions, which run substantially parallel to each other and are substantially aligned, thus form one passage which in this case is non-continuous or is interrupted by an inlay wall 74, which in this example extends substantially in the same direction as the shaft axis SA. It is to be noted that the passage running longitudinally in the elongated connector head could additionally or instead be interrupted by a portion of the connector head to make this passage non-continuous in this manner. The inlay wall is configured to be received in a slot of the connector head when assembled in the connector head. As depicted, the rod fastener 90b is configured to be engaged with the second locking means 32b, and to mate against the spinal rod 100. The elongated connector head as shown in FIGS. 17A to 17D has the advantage that a very short rod end can still be rigidly fixated.

Figure 18A:
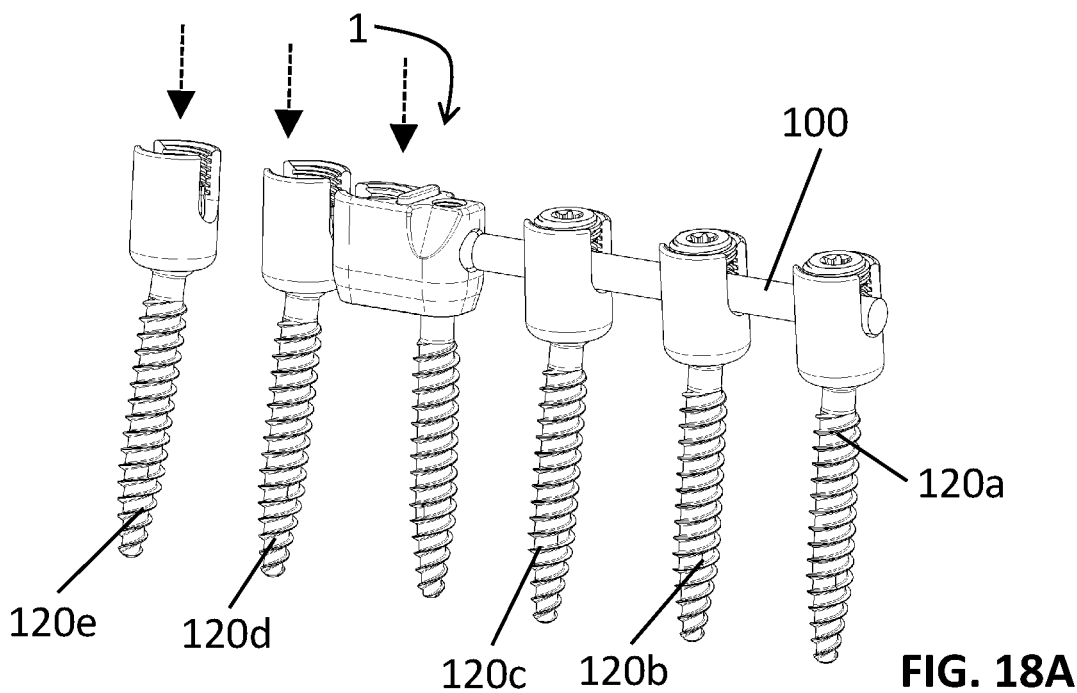
FIGS. 18A to 18D illustrate an example surgical procedure for elongating an existing posterior stabilisation construct by using the bone fastener assembly of FIGS. 17A to 17D.

FIGS. 18A to 18D illustrate an example surgical technique or procedure for elongating an existing posterior stabilisation construct by using the bone fastener assembly 1 of FIGS. 17A to 17D. For illustration purposes, no bony structures are shown. FIG. 18A depicts an implanted, in situ posterior spinal stabilisation construct, including first, second and third state-of-the-art pedicle screws 120a, 120b, 120c, which are connected by a first rod 100. In this illustrative example, the first rod 100 extends beyond the third pedicle screw 120C. In this clinical situation, the in situ construct requires elongation, and it is preferred not to remove any in situ screws or rods. Furthermore, FIG. 18A shows the pedicle screws in place. A bone fastener assembly 1 is placed next to the third pedicle screw 120C. Two more pedicle screws, namely a fourth pedicle screws 120d and a fifth pedicle screw 120e, are placed at the adjacent vertebral levels or in the adjacent vertebral bodies.

Figure 18B:
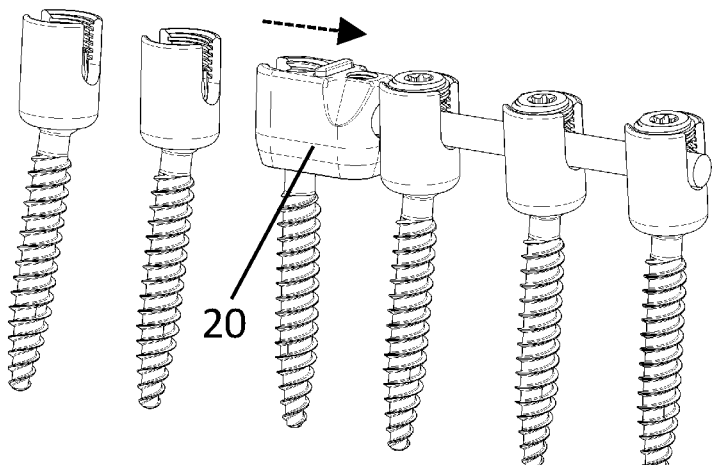
Figure 18C:
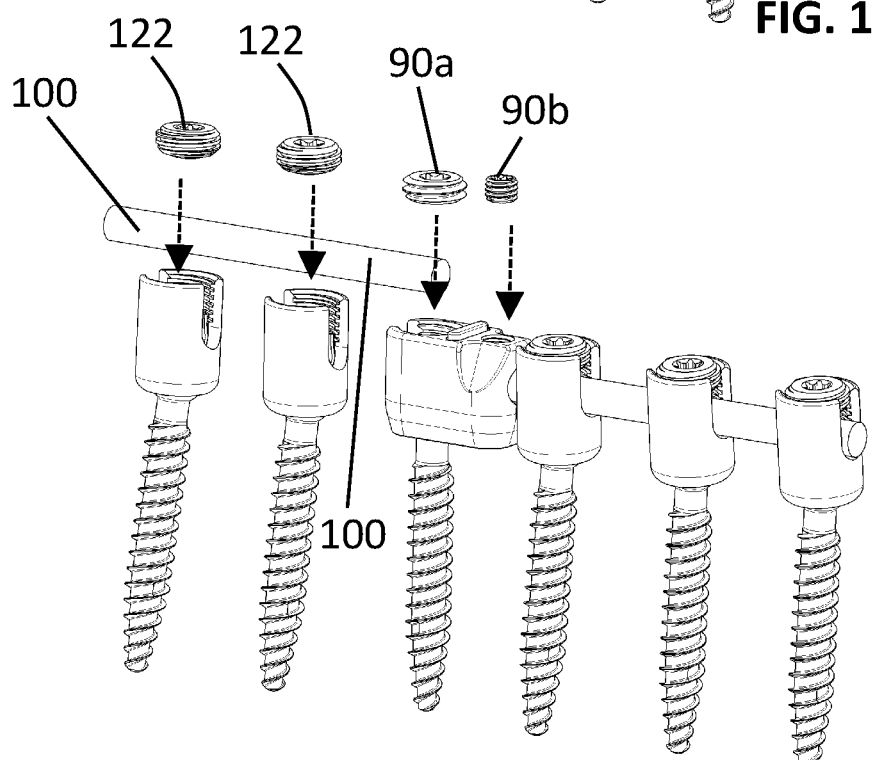
Figure 18D:
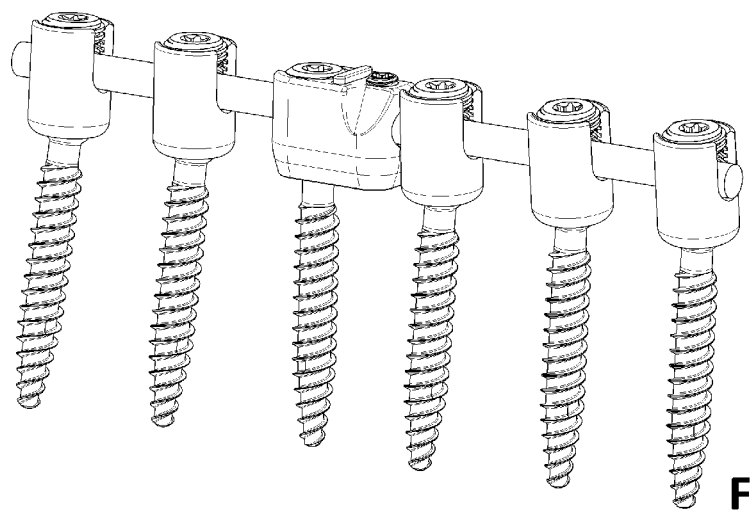

FIG. 18B depicts the elongated connector head 20 being translated over the first rod 100. The end of the first rod 100 is engaged into the bore 118. FIG. 18C depicts the insertion of a second rod 101, and the engagement of the second rod 101 with the bone fastener assembly 1 and with the fourth and fifth pedicle screws 120d, 120e. It further depicts the placement of the rod fasteners 90a and 90b and two set screws 122 to rigidly fixate the extended construct. FIG. 18D depicts the elongated construct.

To summarise the above teachings of the present invention according to one aspect, there is provided a spinal bone fastener assembly 1 for connecting and/or aligning at least a first rod 100 and a second rod 101, the bone fastener assembly comprising a bone fastener 10 having a bone fastener head 12 and a bone fastener shaft 13 with a shaft axis SA, and further comprising an elongated connector head 20 for receiving the first rod and/or the second rod, at least one rod fastener 90a, 90b, at least one bone fastener engaging insert 50 and/or at least one rod receiving inlay 70, the elongated connector head 20 having a head length HL, a head width HW and a head height HH, wherein
  the head width and head height define a first head end 21 and a second, opposite head end 22,
  the head length and head height define a first head side 23 and a second, opposite head side 24,
  the head length and the head width define a head top side 25 and a head bottom side 26,
  and wherein the elongated connector head comprises
  a rod receiving passage 27 extending longitudinally through the elongated connector head between the first and second head ends, or at least two rod receiving passages 27a, 27b extending sideways through the elongated connector head between the first and second head sides,
  a bone fastener head receiving recess 31, which is open to the head bottom side 26, and at least one locking feature 32a, 32b for engaging with the at least one rod fastener 90a, 90b,
  wherein the bone fastener head receiving recess is configured as an elongated or combined elongated channel extending longitudinally within the elongated connector head, and in that the bone fastener head receiving recess has an average channel length CL and an average channel width CW, which is smaller than the average channel length CL, thereby providing at least one translational degree of freedom for the bone fastener 10 along the channel length CL and at least one rotational degree of freedom for the bone fastener 10 about the shaft axis SA.

While the invention has been illustrated and described in detail in the drawings and foregoing description, such illustration and description are to be considered illustrative or exemplary and not restrictive, the invention being not limited to the disclosed embodiments. Other embodiments and variants are understood, and can be achieved by those skilled in the art when carrying out the claimed invention, based on a study of the drawings, the disclosure and the appended claims. New embodiments or variants may be obtained by combining any of the above teachings. For instance, the elongated connector head could comprise more than one passage extending longitudinally through the elongated connector head 20 between the first and second head ends 21, 22, or more than two rod receiving passages 27a, 27b extending sideways through the elongated connector head 20 between the first and second head sides.

In the claims, the word "comprising" or "including" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:
1. A spinal bone fastener assembly for connecting and/or aligning at least a first rod and a second rod, the bone fastener assembly comprising:
  a bone fastener having a bone fastener head and a bone fastener shaft with a shaft axis, and
  the bone fastener assembly further comprising:
    an elongated connector head for receiving the first rod and the second rod,
    at least one rod fastener,
    at least one bone fastener engaging insert, and
    at least one rod receiving inlay, the elongated connector head having a head length, a head width and a head height,
  wherein:
    the head width and head height define a first head end and a second, opposite head end,
    the head length and head height define a first head side and a second, opposite head side,
    the head length and the head width define a head top side and a head bottom side,
    the elongated connector head comprises:
      a rod receiving passage extending longitudinally through the elongated connector head between the first and second head ends, or at least two rod receiving passages extending sideways through the elongated connector head between the first and second head sides,
      a bone fastener head receiving recess, which is open to the head bottom side, and
      at least one locking feature for engaging with the at least one rod fastener, the bone fastener head receiving recess is configured as an elongated or combined elongated channel extending longitudinally within the elongated connector head, the bone fastener head receiving recess has an average channel length and an average channel width, which is smaller than the average channel length, thereby providing at least one translational degree of freedom for the bone fastener along the channel length and at least one rotational degree of freedom for the bone fastener about the shaft axis, the at least one rod receiving inlay is sized and shaped to be received within the elongated connector head, wherein a respective rod receiving inlay comprises at least one rod receiving channel extending along the length or width of the respective rod receiving inlay, and wherein a respective rod receiving channel is sized and shaped to hold the first rod and/or the second rod in a substantially play-free manner.

2. The spinal bone fastener assembly according to claim 1, wherein the translational degree of freedom within the bone fastener head receiving recess defines a translation length of at least 6 mm.

3. The spinal bone fastener assembly according to claim 1, wherein the bone fastener head receiving recess is sized and shaped to directly capture or encompass the bone fastener head in an at least partly form-fit and separation inhibiting manner through the bottom side.

4. The spinal bone fastener assembly according to claim 1, wherein the bone fastener head receiving recess is sized and shaped to capture or encompass the at least one bone fastener engaging insert in an at least partly form-fit manner.

5. The spinal bone fastener assembly according to claim 1, wherein:
the spinal bone fastener assembly further comprises the first rod and/or the second rod, and
the first rod and/or the second rod is/are received in at least one of the passages so that in a locked configuration of the spinal bone fastener assembly:
a respective rod fastener is pressed against a respective rod,
the respective rod is pressed against the respective rod receiving inlay, and
the respective rod receiving inlay is pressed against a respective bone fastener engaging insert, which is pressed against the bone fastener head, which is seated against an inner wall of the bone fastener head receiving recess.

6. The spinal bone fastener assembly according to claim 1, wherein:
the spinal bone fastener assembly further comprises the first rod and/or or the second rod, and
the first rod and/or the second rod is/are received in at least one of the passages so that in a locked configuration of the spinal bone fastener assembly:
a respective rod fastener is pressed against a respective rod,
the respective rod is pressed against the respective rod receiving inlay, and
the respective rod receiving inlay is pressed against the bone fastener head, which is pressed against a respective bone fastener engaging insert, which is seated against an inner wall of the bone fastener head receiving recess.

7. The spinal bone fastener assembly according to claim 1, wherein the elongated connector head comprises a pocket extending between the head top side and the head bottom side, and intersecting the rod receiving passage(s), the at least one locking feature, and the bone fastener head receiving recess.

8. The spinal bone fastener assembly according to claim 1, wherein
the at least one rod receiving channel has at least one first channel width and a second channel width, which is unequal to the first channel width.

9. The spinal bone fastener assembly according to claim 1, wherein
the at least one rod receiving channel defines at least a first channel axis, and
a second channel axis oriented at an obtuse angle with respect to the first channel axis.

10. The spinal bone fastener assembly according to claim 1, wherein the spinal bone fastener assembly comprises a plurality of connected rod receiving inlays in the elongated connector head.

11. The spinal bone fastener assembly according to claim 1, wherein a head length to head width ratio is at least 1.5.

12. The spinal bone fastener assembly according to claim 1, wherein
the at least one rod receiving channel has a channel length and a channel width, and
a channel length to channel width ratio is at least 1.5.

13. The spinal bone fastener assembly according to claim 1, wherein the at least one rod fastener and/or the bone fastener comprise(s) an external thread.

14. The spinal bone fastener assembly according to claim 1, wherein:
the bone fastener head is shaped as a spherical head engaged in the bone fastener head receiving recess shaped substantially in a complementary manner to the spherical head, and
the bone fastener is configured to swivel at least along a longitudinal axis of the connector head within the bone fastener head receiving recess.

15. The spinal bone fastener assembly according to claim 1, wherein the at least one bone fastener engaging insert comprises a bone fastener head engaging recess shaped as an at least partly concave recess, and having an at least partly circular border.

16. The spinal bone fastener assembly according to claim 1, wherein:
a respective rod receiving passage comprises:
a passage start section, and
a passage end section, and
the passage start section is open to the first head side, and the passage end section is open to the second head side, or vice versa.

17. The spinal bone fastener assembly according to claim 1, wherein the at least one bone fastener engaging insert is a disc-shaped element comprising a hole cross-sectionally through the bone fastener engaging insert.

18. The spinal bone fastener assembly according to claim 1, wherein at least one of the two rod receiving passages extending sideways through the elongated connector head between the first and second head sides extends to the first or second head end.

19. The spinal bone fastener assembly according to claim 1, wherein the spinal bone fastener assembly comprises two rod fasteners arranged to be placed side by side in the elongated connector head.

20. The spinal bone fastener assembly according to claim 1, wherein:
the elongated connector head comprises:
a first locking feature configured to engage with a first rod fastener, and
a second locking feature configured to engage with a second rod fastener, and
the first and second locking features are arranged side by side along the longitudinal axis of the elongated connector head.

21. The spinal bone fastener assembly according to claim 1, wherein the at least one bone fastener engaging insert comprises a first insert portion and a second insert portion.

22. The spinal bone fastener assembly according to claim 1, wherein the at least one rod receiving inlay is sized and shaped to receive only one of the first and second rods when assembled in the elongated connector head.

23. The spinal bone fastener assembly according to claim 1, wherein the at least one bone fastener engaging insert comprises at least a first tapered face configured to come in contact with a second tapered face of the elongated connector head when assembled in the elongated connector head.

24. The spinal bone fastener assembly according to claim 1, wherein the rod receiving passage comprises a closed channel portion to form-fittingly engage with the respective rod.

25. The spinal bone fastener assembly according to claim 1, wherein the rod receiving passage extending longitudinally through the elongated connector head is a non-continuous passage.

26. The spinal bone fastener assembly according to claim 1, wherein the elongated connector head comprises:
at least two rod receiving passages extending longitudinally through the elongated connector head between the first and second head ends, or
at least two rod receiving passages extending sideways through the elongated connector head between the first and second head sides.

27. A kit comprising a spinal bone fastener assembly for connecting and/or aligning at least a first rod and a second rod, the bone fastener assembly comprising:
a bone fastener having a bone fastener head and a bone fastener shaft with a shaft axis, and
the bone fastener assembly further comprising:
an elongated connector head for receiving the first rod and the second rod,
at least one rod fastener,
at least one bone fastener engaging insert, and
a plurality of rod receiving inlays for assembly into the elongated connector head, the elongated connector head having a head length, a head width and a head height,
wherein:
the head width and head height define a first head end and a second, opposite head end,
the head length and head height define a first head side and a second, opposite head side,
the head length and the head width define a head top side and a head bottom side,
the elongated connector head comprises:
a rod receiving passage extending longitudinally through the elongated connector head between the first and second head ends, or at least two rod receiving passages extending sideways through the elongated connector head between the first and second head sides,
a bone fastener head receiving recess, which is open to the head bottom side, and
at least one locking feature for engaging with the at least one rod fastener,
the bone fastener head receiving recess is configured as an elongated or combined elongated channel extending longitudinally within the elongated connector head, and
the bone fastener head receiving recess has an average channel length and an average channel width, which is smaller than the average channel length, thereby providing at least one translational degree of freedom for the bone fastener along the channel length and at least one rotational degree of freedom for the bone fastener about the shaft axis,
wherein
the plurality of rod receiving inlays comprise rod receiving channels of different widths.

28. A method for connecting a bone fastener assembly to an implanted spinal construct comprising a plurality of first bone fasteners and a stabilisation rod connected to the plurality of first bone fasteners, the bone fastener assembly comprising a second bone fastener having a bone fastener head and a bone fastener shaft, an elongated connector head comprising a bone fastener head receiving recess for receiving the bone fastener head configured to translate within the bone fastener head receiving recess in an unlocked state, at least one bone fastener engaging insert, and at least one rod receiving inlay, the elongated connector head having a head length, a head width and a head height, wherein the head width and head height define a first head end and a second, opposite head end, the head length and head height define a first head side and a second, opposite head side, the head length and the head width define a head top side and a head bottom side, the elongated connector head comprising: a rod receiving passage extending longitudinally through the elongated connector head between the first and second head ends, or at least two rod receiving passages extending sideways through the elongated connector head between the first and second head sides, the at least one rod receiving inlay being sized and shaped to be received within the elongated connector head, wherein a respective rod receiving inlay comprises at least one rod receiving channel extending along the length or width of the respective rod receiving inlay, and wherein a respective rod receiving channel is sized and shaped to hold the first rod and/or the second rod in a substantially play-free manner, the method comprising:
implanting the bone fastener assembly to a target bone;
sliding the elongated connector head towards the stabilisation rod to thereby translate the elongated connector head with respect to the implanted second bone fastener so that a portion of the elongated connector head is placed under the stabilisation rod such that the respective rod receiving channel holds the stabilisation rod in a substantially play-free manner; and
placing a rod fastener into the elongated connector head to fix the stabilisation rod to the elongated connector head.

29. The method according to claim 28, wherein the elongated connector head is slid substantially parallel with respect to a longitudinal axis of the stabilisation rod, or wherein the elongated connector head is slid substantially orthogonally with respect to a longitudinal axis of the stabilisation rod.

* * * * *